（12）United States Patent
Grobshtein et al.

(10) Patent No.: US 9,579,072 B1
(45) Date of Patent: Feb. 28, 2017

(54) SYSTEMS AND METHODS FOR IMAGING WITH MULTI-HEAD CAMERA

(71) Applicant: General Electric Company, Schenectady, NY (US)

(72) Inventors: Yariv Grobshtein, Tirat Carmel (IL); Shiran Golan, Tirat Carmel (IL); Yaron Hefetz, Tirat Carmel (IL); Gil Kovalski, Tirat Carmel (IL); Jean-Paul Bouhnik, Tirat Carmel (IL); Michael Kogan, Tirat Carmel (IL); Sergio Steinfeld, Tirat Carmel (IL); Michael Gaisinsky, Tirat Carmel (IL); Avi Bar-Shalev, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 22 days.

(21) Appl. No.: 14/871,091

(22) Filed: Sep. 30, 2015

(51) Int. Cl.
*A61B 6/03* (2006.01)
*A61B 6/00* (2006.01)
*A61B 6/04* (2006.01)

(52) U.S. Cl.
CPC ............ *A61B 6/037* (2013.01); *A61B 6/0407* (2013.01); *A61B 6/4435* (2013.01); *A61B 6/461* (2013.01)

(58) Field of Classification Search
CPC ...... A61B 6/037; A61B 6/0407; A61B 6/4435
See application file for complete search history.

(56) References Cited

U.S. PATENT DOCUMENTS

| 5,825,031 | A | * | 10/1998 | Wong | ..................... | G01T 1/164 |
| | | | | | | 250/363.03 |
| 8,542,892 | B2 | * | 9/2013 | Kovalski | ............... | G06T 7/0028 |
| | | | | | | 378/4 |
| 9,029,791 | B1 | | 5/2015 | Kovalski et al. | | |
| 9,084,542 | B2 | | 7/2015 | Bouhnik et al. | | |
| 2007/0232881 | A1 | * | 10/2007 | Shai | ..................... | A61B 6/0457 |
| | | | | | | 600/407 |
| 2015/0094573 | A1 | | 4/2015 | Bouhnik et al. | | |

(Continued)

OTHER PUBLICATIONS

International Search Report and Written Opinion for corresponding PCT application No. PCT/US2016/038375 mailed Oct. 18, 2016; 11 pages.

(Continued)

*Primary Examiner* — Casey Bryant
(74) *Attorney, Agent, or Firm* — Dean D. Small; The Small Patent Law Group, LLC

(57) ABSTRACT

Nuclear medicine (NM) multi-head imaging system includes a plurality of detector units coupled to a gantry. The detector units configured to face toward a center of the bore and including a series of first detector units and a second detector unit. The system also includes at least one processor that, when executing programmed instructions, performs the following operations. The at least one processor rotates the first detector units such that the first detector units face in a common first direction that is generally toward the bore. A working gap exists between the detector FOVs of the respective first detector units. The at least one processor rotates the second detector unit such that the second detector unit faces in a second direction that is opposite the first direction. The detector FOV of the second detector unit covers the working gap.

15 Claims, 16 Drawing Sheets

(56) References Cited

U.S. PATENT DOCUMENTS

| | | | |
|---|---|---|---|
| 2015/0173696 A1* | 6/2015 | Zingerman | A61B 6/035 378/9 |
| 2015/0177939 A1 | 6/2015 | Anderson et al. | |
| 2015/0257719 A1* | 9/2015 | Shai | A61B 6/032 600/436 |
| 2016/0081635 A1* | 3/2016 | Divine | A61B 6/06 378/19 |

OTHER PUBLICATIONS

U.S. Appl. No. 14/788,180, entitled "Systems and Methods for Dynamic Scanning With Multi-Head Camera," filed Jun. 30, 2015; 49 pages.

Bellevre et al.; First determination of the heart-to mediastinum radio using cardiac dual isotope (123 I-MIBG/ 99m Tc-tetrofosmin) CZT imaging in patients with heart failure; the ADRECARD study;Eur J. Nucl. Med. Mol. Imaging; Jul. 31, 2015; 8 pages.

* cited by examiner

SYSTEMS AND METHODS FOR IMAGING WITH MULTI-HEAD CAMERA

BACKGROUND

The subject matter disclosed herein relates generally to imaging systems, and more particularly to nuclear medical imaging systems having multi-head detectors.

In nuclear medicine (NM) imaging, such as single photon emission computed tomography (SPECT) or positron emission tomography (PET) imaging, radiopharmaceuticals are administered internally to a patient. The radiopharmaceuticals emit radiation that may be captured by an NM imaging system to generate images for diagnostic review. The NM imaging system may be configured as a multi-head system having a number of individual detectors (or gamma cameras) that are distributed about a bore of the gantry. The detectors are spaced apart from each other such that gaps exist between adjacent detectors. Each detector may be configured to move to provide a range over which the detector may acquire image data.

Prior to the imaging session in which the diagnostic images are obtained, the patient is positioned relative to the detectors so that a collective field-of-view of the NM imaging system includes the anatomical region of interest (e.g., heart, brain, etc.). At this time, one or more persistence images are obtained and reviewed to position the patient. The persistence images are typically only used to position the patient and, as such, have a lower quality than the images used for diagnosis. Persistence images may be acquired at a frequency of, for example, one image per second or less. As the images are acquired, the technician reviews the images and incrementally moves the patient within the bore of the gantry so that the anatomical region-of-interest is within the collective field-of-view. It is generally desirable to quickly position the patient, because the emissions from the radioisotopes reduce over time. During the time in which persistence images are acquired, a technician may also assess the activity of the radioisotopes for determining the scan duration It can be challenging, however, to use persistence images from multi-head imaging systems. For example, gaps may exist between adjacent detectors thereby rendering it more difficult to identify the anatomical region of interest in the persistence images. This process is made even more difficult for field-of-views that are only slightly larger than the anatomical region of interest.

BRIEF DESCRIPTION

In an embodiment, a nuclear medicine (NM) multi-head imaging system is provided that includes a gantry defining a bore configured to accept an object to be imaged. The system also includes a plurality of detector units coupled to the gantry. The detector units are configured to face toward a center of the bore and have respective detector field-of-views (FOVs). Each of the detector units is configured to rotate about a unit axis. The plurality of detector units include a series of first detector units and a second detector unit. The system also includes at least one processor configured to execute programmed instructions stored in memory, wherein the at least one processor, when executing the programmed instructions, performs the following operations. The at least one processor rotates the first detector units such that the first detector units face in a common first direction that is generally toward the bore. A working gap exists between the detector FOVs of the respective first detector units. The at least one processor rotates the second detector unit such that the second detector unit faces in a second direction that is opposite the first direction. The detector FOV of the second detector unit covers the working gap.

In an embodiment, a method of imaging an object within a bore of a nuclear medicine (NM) imaging system is provided. The NM imaging system includes a plurality of detector units that are distributed about the bore and that each include a detector field-of-view (FOV). The plurality of detector units include a first series of first detector units and a second detector unit. The method includes positioning an object onto a table within the bore of the NM imaging system and moving the table to a designated position. Using at least one processor, the method also includes rotating the first detector units to face in a common first direction that is generally toward the bore. A working gap exists between the detector FOVs of the respective first detector units. The method also includes rotating the second detector unit to face in a second direction that is opposite the first direction. The detector FOV of the second detector unit includes the working gap. The method also includes acquiring image data from the first and second detector units and generating a composite persistence image based on the image data. The method also includes adjusting the position of the table within the bore based on the composite persistence image.

In an embodiment, a nuclear medicine (NM) multi-head imaging system is provided that includes a gantry defining a bore and a table positioned within the bore and configured to support an object to be imaged. The system also includes a plurality of detector units coupled to the gantry. Each of the detector units is configured to face toward a center of the bore and have a respective detector field-of-view (FOV). Each of the detector units is configured to rotate about a unit axis. The plurality of detector units include first and second detector units. The system also includes at least one processor configured to execute programmed instructions stored in memory. The at least one processor, when executing the programmed instructions, performs the following operations. The at least one processor rotates the first and second detector units as the first and second detector units acquire image data and generates a composite persistence image based on the image data. The table is configured to be moved within the bore in response to inputs from a user or commands from the at least one processor.

DETAILED DESCRIPTION

Figure 1:
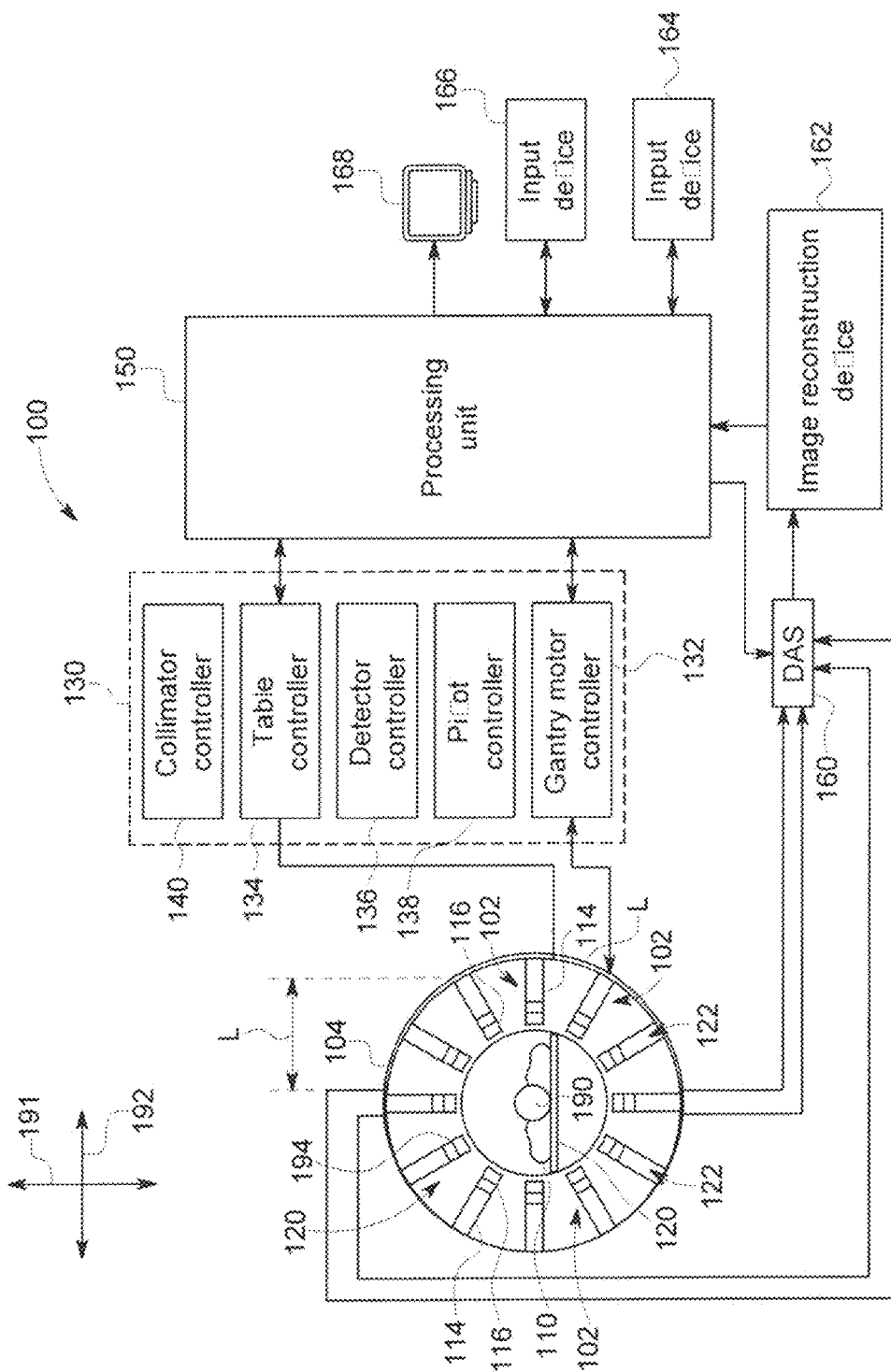
FIG. 1 provides a schematic view of a nuclear medicine (NM) imaging system in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, phrases such as "a plurality of [elements]" and the like, when used in the description and claims, do not necessarily refer to each and every element that a system may have. The system may have other elements that are similar to the plurality of elements but do not have the same features or limitations. For example, the phrase "a plurality of detector units [being/having a recited feature or limitation]" does not necessarily mean that each and every detector unit of the system has the recited feature or limitation. Other detector units may not include the recited feature or limitation. Similarly, phrases such as "each of the detector units [being/having a recited feature or limitation]" and the like, when used in the description and claims, does not preclude the possibility that the system may have other detector units. Accordingly, unless explicitly stated otherwise (e.g., "each and every detector unit of the system"), embodiments may include similar elements that do not have the recited features or limitations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments set forth herein include nuclear medicine (NM) multi-head imaging systems, which are hereinafter referred to as NM imaging systems, methods of acquiring NM images, and computer readable media having one or more software modules that direct one or more processors to execute the methods described herein. Embodiments described herein and illustrated by the figures may be implemented in imaging systems, such as, for example, single photon emission computed tomography (SPECT), SPECT computed tomography (SPECT-CT), positron emission tomography (PET), and PET-CT.

A technical effect of at least one embodiment includes acquiring persistence images (referred to as composite persistence images) from an NM imaging system having a plurality of detector units that are distributed about a center of the bore of the NM imaging system. The NM imaging system may include several detectors units. For example, the NM imaging system may have 12 detector units, although it is contemplated that the NM imaging may include more or fewer detector units. At least some of the detector units may be movable in a radial direction (e.g., generally toward or away from a longitudinal axis extending through the bore) and rotatable about a respective unit axis that extends parallel to the longitudinal axis. The detector units may also be moved as a group. For example, a set of detector units may be rotated as a group about the longitudinal axis. In some embodiments, only a select number of the detector units (e.g., 3, 4, 5, 6, or 7 detectors units) may be used to obtain the persistence images. For example, embodiments may move the detector units closer to or away from the bore and rotate the detector units about the respective unit axes such that the detector units generally oppose each other across the bore with the object therebetween.

The detector units may have respective detector field-of-views (FOVs). For some embodiments, a technical effect includes generating a composite persistence image that is based on image data from a plurality of detectors units in which some of the detector units face in one direction and at least one other detector unit faces in an opposite direction. In such instances, the detector FOVs may be interleaved with respect to one another. The composite persistence image may "fill" any gaps between adjacent detector units using image data from the detector unit(s) that generally oppose the other detector units. The persistence images may enable a technician to better position the object for imaging.

For some embodiments, a technical effect includes generating a composite persistence image that is based on image data from a plurality of detector units in which each of the detector units acquires a series of projections. Each projection corresponds to a different rotational position of the detector unit. The series of projections may be combined (e.g., side-by-side) to form the composite persistence image.

For some embodiments, a technical effect includes enabling an operator or technician to more quickly identify a region of interest (ROI) or multiple ROIs from a single object. For example, embodiments may include user interfaces that provide a better or more efficient workflow.

As used herein, the term "composite persistence image" means an image that may be reviewed or analyzed by a technician or a system for locating an object at a designated position in the bore. Unlike planar persistence images that are based on image data acquired from one side of the object, the composite persistence images may appear like planar images, but are based on image data that was obtained on opposite sides of the object. As such, the composite persistence images may be referred to as pseudo-planar persistence images. The composite persistence images are typically of a lower quality compared to diagnostic images.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical.

It should be noted that the arrangement of FIG. 1 is provided by way of example for illustrative purposes, and that other arrangements may be employed in various embodiments. In the illustrated example, the imaging system 100 includes a plurality of detector assemblies 102 that are coupled (e.g., mounted) to a gantry 104 that defines a bore 118 of the imaging system 100. The imaging system 100 may also include a table 120 that is positioned within the bore 118. The table 120 is configured to support an object 110, such as a patient. The detector assemblies 102 are positioned circumferentially about the bore 118. The detector assemblies 102 may be positioned within the gantry 104 such that the detector assemblies 102 are not visible to the patient or, alternatively, at least a portion of the detector assemblies 102 may be exposed within the bore 118.

In the illustrated embodiment, each detector assembly 102 includes an arm 114 and a head 116. The head 116 includes at least one detector unit 115. The head 116 is disposed at a radially inward end of the arm 114. The arm 114 is configured to move the head 116 radially toward and/or away from a center of the bore 118 (and/or in other directions) and thereby move the corresponding detector unit(s) 115. A detector unit 115 may have a relative position with respect to the bore 118 or a central longitudinal axis 190 that extends through the bore 118. The relative position may include a spatial location (e.g., coordinates in an X, Y, Z space) and an orientation (e.g., rotational position or orientation). For example, the relative position of each detector unit 115 may be defined by (1) a rotational orientation or position of the plurality of detector units 115; (2) a radial position of the corresponding detector unit 115; and (3) a rotational position or orientation of the corresponding detector unit 115.

Each of (1), (2), and (3) may be identified or determined by the imaging system. To this end, the imaging system and/or the detector units may include encoders that identify (1), (2), or (3). For example, each of the arms 114 may include or be operably coupled to a motor that selectively controls the position of the head 116 relative to the bore 118. When the head 116 is moved, information relating to the state of the motor may identify the radial position of the detector unit. As another example, each of the detector units 115 may be secured to a common ring (not show) that is capable of rotating about the longitudinal axis 190. An encoder may identify the rotational position of the ring (e.g., in degrees or radians) that may be used to identify the relative position of each of the detector units. As another example, the head 116 may be configured to pivot or rotate about a unit axis 194. The head 116 may be operably coupled to a motor that selectively controls the rotational position of the head 116. When the head 116 is rotated, information relating to the state of the motor may identify the rotational position of the corresponding detector unit.

The detector unit 115 may be, for example, a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. The detector unit 115 may be particularly configured for use with, for example, nuclear medicine (NM) imaging systems, positron emission tomography (PET) imaging systems, and/or single photon emission computed tomography (SPECT) imaging systems.

Each of the detector units 115 in various embodiments is smaller than a conventional whole body or general purpose imaging detector. A conventional imaging detector may be large enough to image most or all of a width or length of a patient's body at one time and may have a diameter or a larger dimension of approximately 50 cm or more. In contrast, each of the detector units 115 may have dimensions of, for example, 4×20 cm and may be formed of Cadmium Zinc Telluride (CZT) tiles or modules. As another example, each of the detector units 115 may be 8×8 cm in size and be composed of a plurality of CZT pixelated modules (not shown). For example, each module may be 4×4 cm in size and have 16×16=256 pixels (pixelated anodes). In some embodiments, each detector unit 115 includes a plurality of modules, such as an array of 1×7 modules. However, different configurations and array sizes are contemplated including, for example, detector units 115 having multiple rows of modules.

Each of the detector units 115 has a detector surface or face, which is directed towards the object 110 or an (ROI) within the object 110. It should be understood that the detector units 115 may be different sizes and/or shapes with respect to each other, such as square, rectangular, circular or other shape. An actual FOV of each of the detector units 115 may be directly proportional to the size and shape of the respective detector unit. The detector units 115 are arranged in a set or array 120. The set 120 may be rotated as a group about the bore 118 or, more specifically, about the longitudinal axis 190. Accordingly, each of the detector units 115 may be selectively rotated about the longitudinal axis 190, selectively moved radially toward or away from the longitudinal axis 190, and be selectively rotated about a respective unit axis 194 that extends parallel to the longitudinal axis 190. As used herein, an element or component is "selectively rotatable," "selectively movable," and the like if the element or component may be controlled in a manner that is different with respect to similar elements or components. For example, one detector unit may be rotated 15° and another detector unit may be rotated 10. The phrases do not require, however, the each element or component be controlled differently. Instead, the terms "selective" or "selectively" only acknowledge that the element or component may be controlled differently.

The table 120 is configured with a support mechanism (not shown) to support and carry the object 110 in one or more of a plurality of viewing positions within the bore 118 and relative to the detector units 115. For example, the table 120 may be operably coupled to one or more motors (not shown). The motors may be configured to move the table 120 along the longitudinal axis 190, along an elevation axis 191, and also along a lateral axis 192. The axes 190-192 are mutually perpendicular. As such, the table 120 and the corresponding motors may selectively position the object 110 within the bore 118. As described above with respect to the detector units, an encoder or other device may determine a position of the table 120 within the bore 118.

In the illustrated embodiment, the gantry 104 is circular or donut-shaped. In other embodiments, however, the gantry 104 may be configured to have other shapes. For example, the gantry 104 may be formed as a closed ring or circle, or as an open arc or arch which allows the object 110 to be easily accessed while imaging and facilitates loading and unloading of the object 110. The gantry 104 may be rotated about the longitudinal axis 190.

Optionally, for embodiments employing one or more parallel-hole collimators, multi-bore collimators may be constructed to be registered with pixels of the detector units 115, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the table 120, the detector units 115, the gantry 104 and/or the collimators 122. The controller unit 130 may have a gantry motor controller 132, a table controller 134, a detector controller 136, a pivot controller 138, and a collimator controller 140. The controllers 130, 132, 134, 136, 138, 140 may be automatically commanded by a processor (or processing unit) 150, manually controlled by an operator, or a combination thereof. The controllers 130, 132, 134, 136, 138, 140 may be part of a processor 150.

The gantry motor controller 132 may move the detector units 115 with respect to the object 110, for example, individually, in segments or subsets, or simultaneously in a fixed relationship to one another. For example, in some embodiments, the gantry controller 132 may cause the detector units 115 and/or support members to move relative to or rotate about the object 110, which may include motion of less than or up to 180° (or more).

The table controller 134 may move the table 120 to position the object 110 relative to the detector units 115. The table 120 may be moved in up-down directions along the elevation axis 191, in-out directions along the longitudinal axis 190, and right-left directions along the lateral axis 192, for example. The detector controller 136 may control movement of each of the detector units 115 to move together as a group or individually. The detector controller 136 also may control movement of the detector units 115 in some embodiments to move closer to and farther from a surface of the object 110, such as by controlling translating movement of the detector units 115 linearly towards or away from the object 110 (e.g., sliding or telescoping movement).

The pivot controller 138 may control the pivoting or rotating movement of the detector units 115. For example, one or more of the detector units 115 or heads 116 may be rotated about a unit axis 194 to view the object 110 from a plurality of angular orientations to acquire, for example, image data for persistence images. The detector units 115 may also be selectively controlled to obtain diagnostic 3D image data in a 3D SPECT or 3D imaging mode of operation. The collimator controller 140 may adjust a position of an adjustable collimator, such as a collimator with adjustable strips (or vanes) or adjustable pinhole(s).

It should be noted that motion of one or more detector units 115 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the object 110 or a portion of the object 110, the detector units 115, the gantry 104, the table 120 and/or the collimators 122 may be adjusted, such as to first or initial imaging positions, as well as subsequent imaging positions. The detector units 115 may each be positioned to image a portion of the object 110. Alternatively, for example in a case of a small size object 110, one or more of the detector units 115 may not be used to acquire data. Positioning may be accomplished manually by the operator and/or automatically, which may include using, for example, image data such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 115 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the detector units 115, the gantry 104, the table 120, and/or the collimators 122 are positioned, image data may be acquired for generating the composite persistence images. After the table 120 (or object 110) is positioned, the detector units 115, the gantry 104, the table 120, and/or the collimators 122 may be positioned to acquire three-dimensional (3D) SPECT images. The image data acquired by each detector unit 115 may be combined and reconstructed into a composite image or 3D images in various embodiments.

In various embodiments, a data acquisition system (DAS) 160 receives electrical signal data produced by the detector units 115 and converts this data into digital signals for subsequent processing. However, in various embodiments, digital signals are generated by the detector units 115. An image reconstruction device 162 (which may be a processing device or computer) and a data storage device 164 may be provided in addition to the processor 150. It should be noted that one or more functions related to one or more of data acquisition, motion control, data processing and image reconstruction may be accomplished through hardware, software, and/or by shared processing resources, which may be located within or near the imaging system 100, or may be located remotely. Additionally, a user input device 166 may be provided to receive user inputs (e.g., control commands), as well as a display 168 for displaying screens to the user. The DAS 160 receives the acquired image data from the detector units 115 together with the corresponding lateral, vertical (or elevational), rotational, and swiveling coordinates of the gantry 104, the detector units 115, and heads 116 for accurate reconstruction of images.

In various embodiments, the detector unit may include an array of pixelated anodes, and may generate different signals depending on the location of where a photon is absorbed in the volume of the detector under a surface of the detector. The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to construct an image or a composite image.

Figure 2:
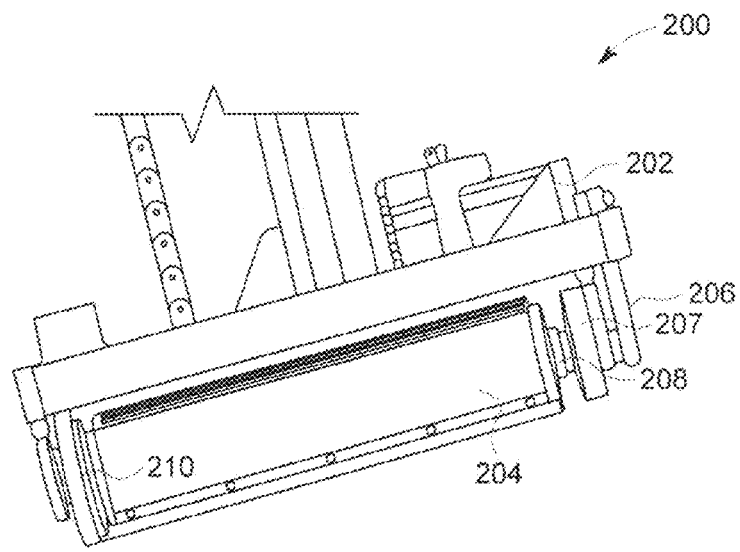
FIG. 2 provides a perspective view of a detector head in accordance with an embodiment.
Figure 3:
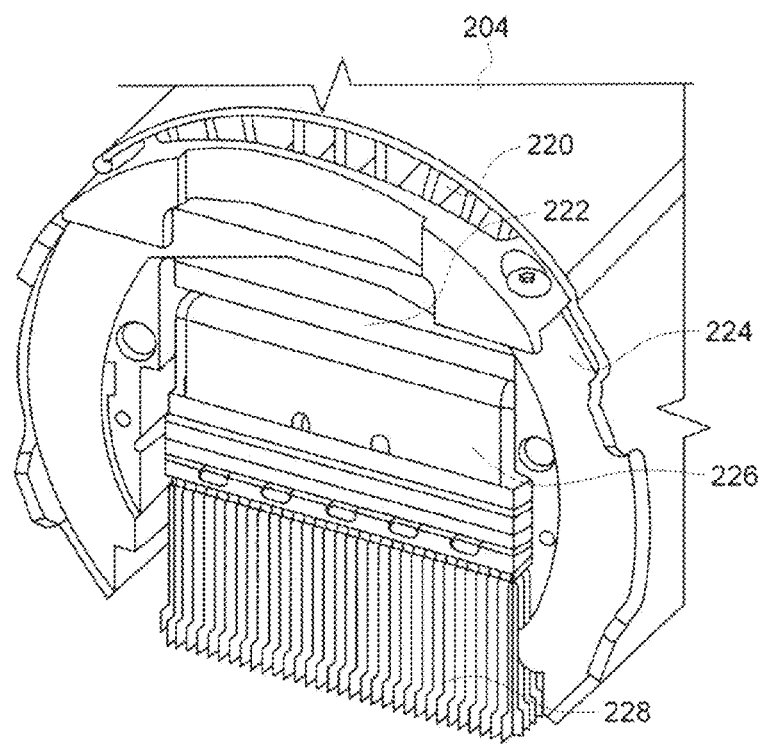
FIG. 3 shows a sectional view of the detector head of FIG. 2.

FIG. 2 is a perspective view of a detector head 200 formed in accordance with various embodiments, and FIG. 3 is a sectional view of the detector head 200. As shown in FIG. 2, the detector head 200 includes a stepper motor 202 that may be utilized to pivot a detector column 204. It may be noted that motors other than stepper motors may be used in various embodiments. Generally, "step-and-shoot" motion may be employed in various embodiments. In step-and-shoot motion, the detector is rapidly pivoted, and then remains stationary during data collection. Step-and-shoot motion may be utilized in various embodiments to eliminate or reduce power transients and/or other electronic noise associated with activation of electrical motors. Use of step-and-shoot motion may also be utilized to eliminate orientation uncertainties associated with each collected photon.

However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector column 204, for example, may include a shield, a processing board, a detector (e.g., a CZT detector) and a collimator. The detector head 200 also includes a gear 206 coupling the stepper motor to the column 204, as well as a slip ring 207 (configured to allow for transfer of signals between the rotating detector column 204 and non-rotating components) and a multiplex board 208. In the illustrated embodiment, the detector head 200 also includes an air channel 210 configured to provide cooling to components of the detector head 200. Also shown in FIG. 3, the detector column 204 includes a heat sink 220, a printed circuit board 222 (which may incorporate one or more aspects of the processing unit 120), a lead shielding 224, a CZT detector module 226, and a collimator 228 that is registered to the CZT detector module 226 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is incorporated herein by reference in its entirety.

Figure 4:
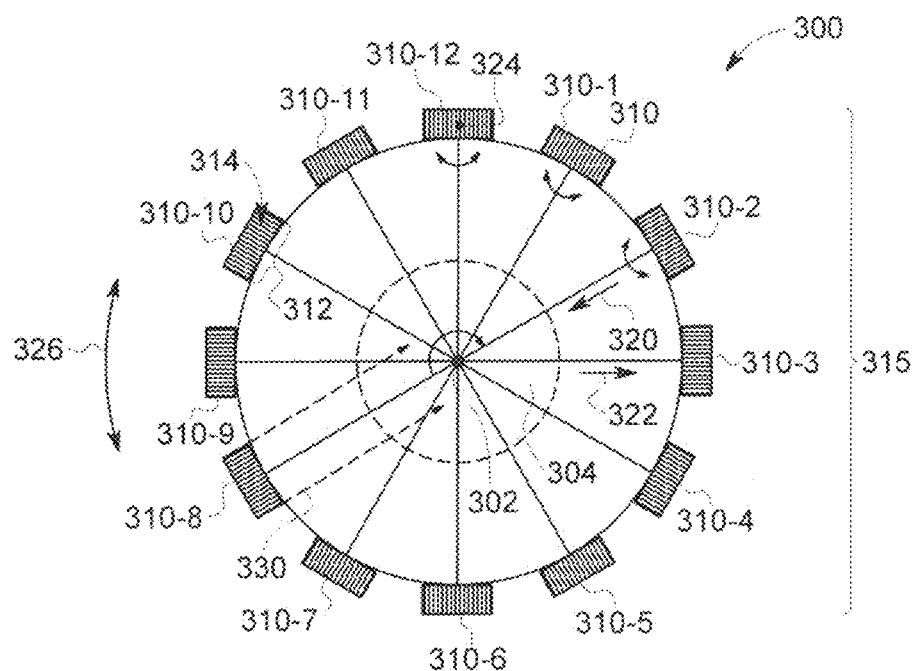
FIG. 4 illustrates an arrangement of detector units (referred to as an imaging arrangement) in accordance with an embodiment.

FIG. 4 illustrates an imaging arrangement 300 of an imaging system (not shown) formed in accordance with an embodiment. The imaging system may be similar or identical to the imaging system 100 (FIG. 1). As shown, a central longitudinal axis 302 extends into and out of the page. The longitudinal axis 302 may extend lengthwise through a center of a bore 304 (indicated by dashed line) of a gantry (not shown). The imaging arrangement 300 includes a plurality of detector units 310. Each of the detector units 310 includes a detection or acquisition surface 312 and a collimator 314.

The detector units 310 form a set or array 315 of detector units 310. In the illustrated embodiment, each of the detector units 310 is configured to be (a) moved in a radially-inward direction 320 or a radially-outward direction 322 and (b) rotated about a respective unit axis 324 that extends through the respective detector unit 310 and parallel to the longitudinal axis 302. In the illustrated embodiment, the set 315 of the detector units 310 is configured to be rotated in a clockwise and/or counter-clockwise direction about the longitudinal axis 302 as indicated by the bi-directional arrow 326. As such, the set 315 of the detector units 310 may have a variety of imaging arrangements in which each imaging arrangement has a different combination of relative positions of the detector units 310. The imaging arrangement 300 is only one of these imaging arrangements. The imaging arrangement may be selected based on, for example, the size and shape of the object and/or the ROI to be imaged. As set forth herein, the detector units 310 of the set 315 may be selectively controlled such that each of detector units 310 may be moved to a designated relative position.

In the illustrated embodiment, the set 315 includes detector units 310-1, 310-2, 310-3, 310-4, 310-5, 310-6, 310-7, 310-8, 310-9, 310-10, 310-11, and 310-12. The detector units 310 are disposed about and oriented to face generally toward the bore 304 and the longitudinal axis 302. The detector units 310 are configured to face generally toward the bore 304 when an object, such as an individual, is positioned within the bore 304. More specifically, the corresponding detection or acquisition surface 312 for each detector unit 310 and/or the detector FOV of a collimator 314 are oriented toward the object to be imaged in the bore 304.

Each detector unit 310 defines a corresponding detector FOV 330 that is capable of being positioned to include a portion of the bore 304. The detector FOV for each detector unit 310, for example, may be aligned along a central axis of a corresponding arm (e.g., arm 114 (FIG. 1)) of the detector unit 310. In the illustrated embodiment, each of the detector units 310 defines a respective detector FOV 330. The detector FOV 330 is indicated by dashed lines that are substantially parallel to each other. However, it should be understood that the 3D spaces acquired by the detector FOVs 330 are not necessarily parallelepipeds or 3D spaces with parallel sides. More specifically, emissions from radioisotopes may enter the holes of the collimator 314 at non-orthogonal angles with respect to the detector surface 312 and be detected by the detector unit 310. As such, the 3D space encompassed by a detector FOV may be based on a radial position of the detector unit 310 relative to the object 310. In many cases, the detector FOVs 330 are essentially parallelepipeds.

In some embodiments, a detector unit 310 is capable of sweeping (e.g., rotating or pivoting) and thereby sweeping the corresponding detector FOV 330. The sweeping may be limited to a sweep range (e.g., 0°-110°). Thus, each detector unit 310 may collect image data over a range that is larger than the respective detector FOV defined by a stationary detector unit. It may be noted that, generally, the sweep range that a detector may rotate within may be larger than the corresponding detector FOV during acquisition. In some cameras, the sweep range that a detector may rotate may be unlimited (e.g., the detector may pivot a full 360 degrees). In some embodiments, such as those described with respect to FIGS. 8 and 9, the detector FOV may be swept to acquire persistence images. In other embodiments, such as those described with respect to FIGS. 5-7, the detector FOVs are not swept to acquire persistence images.

Figure 5:
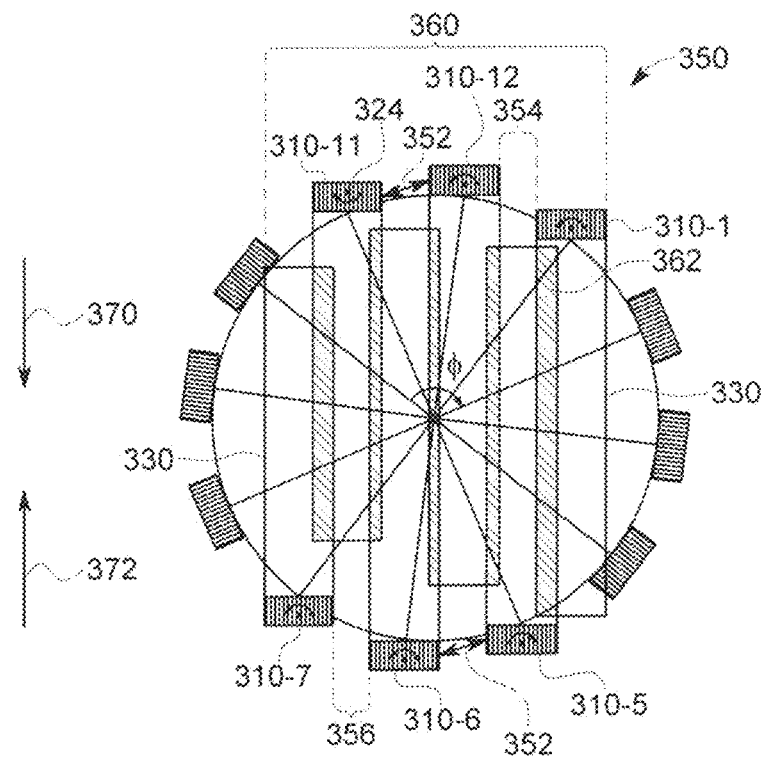
FIG. 5 illustrates the detector units of FIG. 4 in a different imaging arrangement to acquire image data for generating a composite persistence image along one anatomical plane.

FIG. 5 illustrates an imaging arrangement 350 that includes the set 315 of the detector units 310. Compared to FIG. 4, the set 315 has a different rotational position. More specifically, the set 315 may have a first rotational position in FIG. 4, but a second rotational position in FIG. 5. Because the set 315 has a different rotational position, the set 315 forms a different imaging arrangement. In some embodiments, the imaging arrangement 350 is configured to acquire a coronal persistence image.

The set 315 has been rotated Φ degrees, relative to the imaging arrangement 300 in FIG. 4, about the longitudinal axis 302. In the illustrated embodiment, Φ is equal to 7.5° but it should be understood that the set 315 may be rotated by a different amount. In order to acquire image data for a composite persistence image, the processor 150 is configured to selectively position a first series of detector units 310, which may be referred to as first detector units in the claims, and a second series of detector units 310, which may be referred to as second detector units in the claims. In the illustrated embodiment, the first series of detector units includes the detector units 310-11, 310-12, and 310-1. The second series of detector units includes the detector units 310-5, 310-6, and 310-7.

A series of detector units typically includes a plurality of detector units that are in order such that each detector unit in the series is adjacent to another detector unit in the series. However, it is not required that a series of detector units include a plurality of detector units that are in order. For instance, if the radial positions of the detector units are immediately adjacent to the bore or the object, it may be possible to use every other detector unit. For example, instead of using detector units 1, 2, 3, only detector units 1 and 3 may be used and detector unit 2 may not be used.

In the illustrated embodiment, each of the detector units 310 in the first and second series has been selectively rotated about the respective unit axis 324. More specifically, the detector unit 310-11 has been rotated 22.5° clockwise (CW), the detector unit 310-12 has been rotated 7.5° counterclockwise (CCW), the detector unit 310-1 has been rotated 37.5° CCW, the detector unit 310-5 has been rotated 22.5° CW, the detector unit 310-6 has been rotated 7.5° clockwise CCW, and the detector unit 310-7 has been rotated 37.5° CCW. The other detector units 310-2, 310-3, 310-4, 310-8, 310-9, and 310-10 have not been selectively rotated and directly face the longitudinal axis 302. In the imaging arrangement 350, the detector surfaces 312 of the first and second series are generally parallel to each other. However, the detector surfaces 312 are not coplanar. In other embodiments, the detector units 310 may be moved radially inward or outward such that the detector surfaces 312 of the first series of detector units 310 are coplanar and/or the detector surfaces 312 of the second series of detector units 310 are coplanar.

As shown in FIG. 5, adjacent detector units 310 are spaced apart by a separation distance 352. In FIG. 5, the separation distances 352 are about equal between the different adjacent detector units 310, but it should be understood that the separation distances 352 may be different for other imaging arrangements. The separation distances 352 between the first series of detector units 310-11, 310-12, and 310-1 cause working gaps 354 between the respective detector FOVs 330. The separation distances 352 between the second series of detector units 310-5, 310-6, and 310-7 cause working gaps 356 between the respective detector FOVs 330.

As shown, the detector units 310 of the second series in FIG. 5 are positioned such that the corresponding detector FOVs 330 acquire image data from a space that is not covered by the detector units 310 of the first series. More specifically, the detector FOV 330 of the detector unit 310-6 is positioned to acquire image data from the working gap 354 between adjacent detector units 310-11 and 310-12. The detector FOV 330 of the detector unit 310-5 is positioned to acquire image data from the working gap 354 between adjacent detector units 310-1 and 310-12. The detector FOV 330 of the detector unit 310-7 is positioned to acquire image data from a space that is adjacent to the detector FOV 330 of the detector unit 310-11.

Likewise, the detector units 310 of the first series in FIG. 5 are positioned such that the corresponding detector FOVs 330 acquire image data from a space that is not covered by the detector units 310 of the second series. In particular, the detector FOV 330 of the detector unit 310-11 is positioned to acquire image data from the working gap 356 between adjacent detector units 310-6 and 310-7. The detector FOV 330 of the detector unit 310-12 is positioned to acquire image data from the working gap 356 between adjacent detector units 310-5 and 310-6. The detector FOV 330 of the detector unit 310-1 is positioned to acquire image data from a space that is adjacent to the detector FOV 330 of the detector unit 310-5.

The detector FOVs 330 form a collective FOV 360. The collective FOV 360 is the space formed from the combined detector FOVs. The collective FOV does not double count overlapping regions 362 between the detector FOVs 330. More specifically, the image data corresponding to the overlapping regions 362 may be modified to adjust for duplicate image data. During a position-determining operation in which the object is positioned relative to the detector units 310, the detector units 310 may acquire image data that is used to generate persistence images. The persistence images may be used by a technician (or automated system) to position the designated ROI with respect to the detector units 310.

The persistence images, however, are composite images based on a select number of detector units 310 in which at least one of the detector units 310 faces in a direction that is opposite the direction of the other detector units 310. More specifically, the detector units 310 of the first series face in a first direction 370 and the detector units 310 of the second series face in a second direction 372. The first and second directions 370, 372 are opposite directions and are generally toward the bore.

Figure 6:
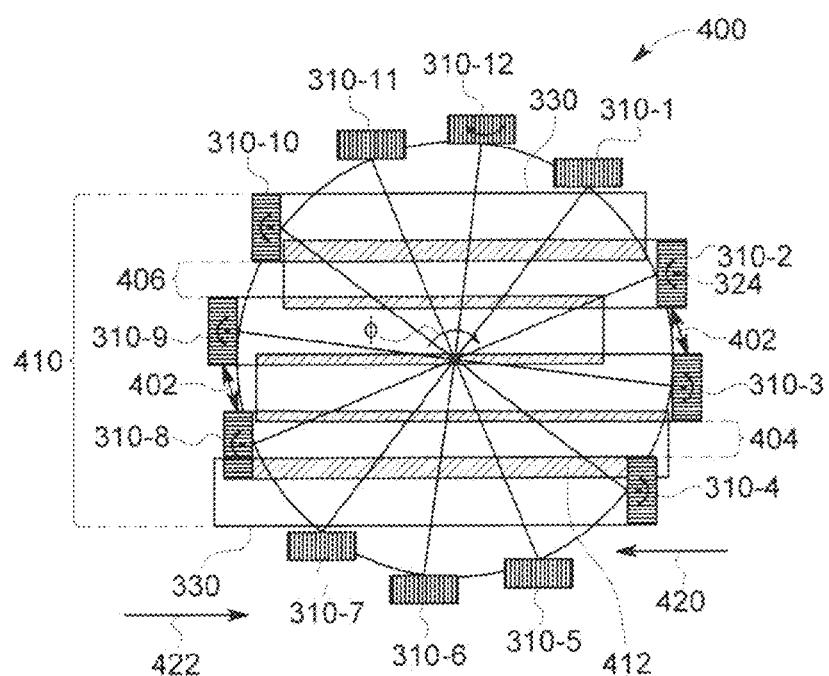
FIG. 6 illustrates the detector units of FIG. 4 in a different imaging arrangement to acquire image data for generating a composite persistence image along one or two anatomical planes.

FIG. 6 illustrates an imaging arrangement 400 that includes the set 315 of the detector units 310. The set 315 has the same rotational position in FIG. 5, but a select number of detector units 310 have been rotated. Accordingly, the imaging arrangement 400 is different from the imaging arrangements 300 (FIG. 4) and 350 (FIG. 5). More specifically, the processor 150 has selectively rotated a third series of detector units 310, which may be referred to as third detector units in the claims, and a fourth series of detector units 310, which may be referred to as fourth detector units in the claims. In the illustrated embodiment, the third series of detector units includes detector units 310-2, 310-3, and 310-4. The fourth series of detector units includes detector units 310-8, 310-9, and 310-10.

In the illustrated embodiment, each of the detector units 310 in the third and fourth series has been selectively rotated about the respective unit axis 324 with respect to a home position. The home position may represent the position at which the detector surface 312 faces the longitudinal axis 302. More specifically, the detector unit 310-2 has been rotated 22.5° CW, the detector unit 310-3 has been rotated 7.5° CCW, the detector unit 310-4 has been rotated 37.5° CCW, the detector unit 310-8 has been rotated 22.5° CW, the detector unit 310-9 has been rotated 7.5° clockwise CCW, and the detector unit 310-10 has been rotated 37.5° CCW. The other detector units 310-11, 310-12, 310-1, 310-5, 310-6, and 310-7 have the same rotational positions relative to the longitudinal axis 302 as shown in FIG. 5.

In the imaging arrangement 400, the detector surfaces 312 of the third and fourth series are generally parallel to each other. However, the detector surfaces 312 are not coplanar. In other embodiments, the detector units 310 may be moved radially inward or outward such that the detector surfaces 312 of the third series of detector units 310 are coplanar and/or the detector surfaces 312 of the fourth series of detector units 310 are coplanar.

As shown in FIG. 6, adjacent detector units 310 are spaced apart by a separation distance 402. The separation distances 402 are about equal between the different adjacent detector units 310 in FIG. 6, but it should be understood that the separation distances 402 may be different for other imaging arrangements. The separation distances 402 between the third series of detector units 310-2, 310-3, and 310-4 cause working gaps 404 between the respective detector FOVs 330. The separation distances 402 between the second series of detector units 310-8, 310-9, and 310-10 cause working gaps 406 between the respective detector FOVs 330.

As shown, the detector units 310 of the fourth series in FIG. 6 are positioned such that the corresponding detector FOVs 330 acquire image data from a space that is not covered by the detector units 310 of the third series. More specifically, the detector FOV 330 of the detector unit 310-8 is positioned to acquire image data from the working gap 404 between adjacent detector units 310-3 and 310-4. The detector FOV 330 of the detector unit 310-9 is positioned to acquire image data from the working gap 404 between adjacent detector units 310-2 and 310-3. The detector FOV 330 of the detector unit 310-10 is positioned to acquire image data from a space that is adjacent to the detector FOV 330 of the detector unit 310-2.

Likewise, the detector units 310 of the third series in FIG. 6 have been positioned such that the corresponding detector FOVs 330 acquire image data from a space that is not covered by the detector units 310 of the fourth series. In particular, the detector FOV 330 of the detector unit 310-2 is positioned to acquire image data from the working gap 406 between adjacent detector units 310-10 and 310-9, and the detector FOV 330 of the detector unit 310-3 is positioned to acquire image data from the working gap 406 between adjacent detector units 310-8 and 310-9. The detector FOV 330 of the detector unit 310-4 is positioned to acquire image data from a space that is adjacent to the detector FOV 330 of the detector unit 310-8.

The select detector FOVs 330 form a collective FOV 410. The collective FOV 410 is the combined detector FOVs that is adjusted for overlapping regions 412 between the detector FOVs 330. As described above with respect to the overlapping regions 362 (FIG. 5), the image data corresponding to the overlapping regions 412 may be modified to account for duplicate image data.

The persistence images obtained from the third and fourth series are composite images that are based on a select number of detector units 310 in which at least one of the detector units 310 faces in a direction that is opposite the direction of the other detector units 310. More specifically, the detector units 310 of the third series face in a third direction 420 and the detector units 310 of the fourth series face in a fourth direction 422. The third and fourth directions 420, 422 are opposite directions.

During some position-determining operations, a technician (or automated system) may review one or more persistence images generated by the imaging arrangement 350 and one or more persistence images generated by the imaging arrangement 400. The imaging arrangement 350 may generate persistence images of a first anatomical plane, such as the coronal plane. The imaging arrangement 400 may generate persistence images of a second anatomical plane, such as the sagittal plane. As shown in FIG. 6, however, the imaging arrangement 400 is also capable of generating persistence images of the coronal plane. Accordingly, a single imaging arrangement may generate persistence images of two anatomical planes. In such embodiments, the technician or automated system may simultaneously analyze composite images of two different anatomical planes while positioning the object relative to the detector units 310.

Figure 7:
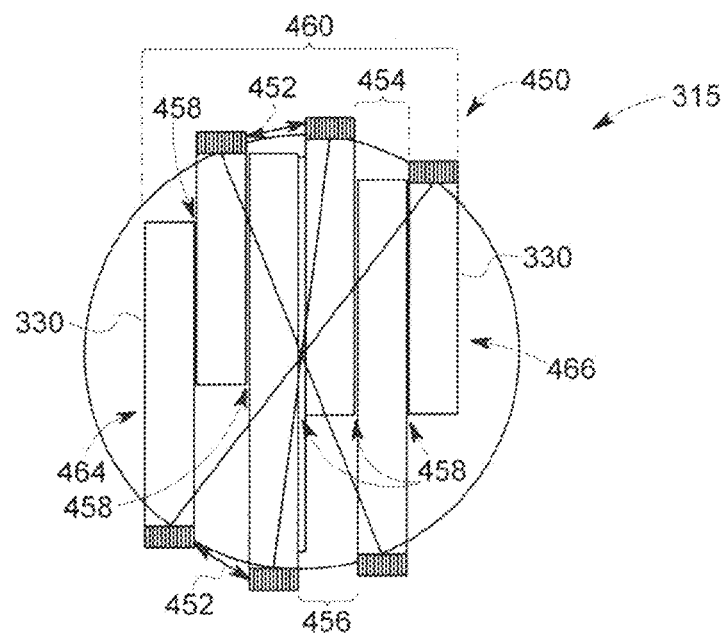
FIG. 7 illustrates the detector units of FIG. 4 in a different imaging arrangement in which working voids exist between corresponding field-of-views (FOVs) of the detector units.

FIG. 7 illustrates an imaging arrangement 450 that includes a select number of the detector units 310 from the set 315. For illustrative purposes, only detector units 310-11, 310-12, 310-1, 310-5, 310-6, and 310-7 are shown, which correspond to the first series of detector units 310 and the second series of detector units 310 described above. The set 315 has the same rotational position as the set 315 shown in FIG. 5. However, compared to FIG. 5, the detector units 310-11, 310-12, 310-1, 310-5, 310-6, and 310-7 have been moved generally away from the bore 304 or generally away from the longitudinal axis 302 such that the detector units 310 have different radial positions. As such, the profile defined by the detector units 310-11, 310-12, 310-1, 310-5, 310-6, and 310-7 has a greater area in FIG. 7 than a profile defined by the same detector units in FIG. 5. Embodiments may increase the profile in order to, for example, accommodate a larger object.

As shown in FIG. 7, adjacent detector units 310 are spaced apart by a separation distance 452. The separation distance 352 (FIG. 5) is less than the separation distance 452. The separation distances 452 between the first series of detector units 310-11, 310-12, and 310-1 cause working gaps 454 between the respective detector FOVs 330. The separation distances 452 between the second series of detector units 310-5, 310-6, and 310-7 cause working gaps 456 between the respective detector FOVs 330.

As shown, the detector units 310 of the second series in FIG. 7 have been positioned such that the corresponding detector FOVs 330 acquire image data from a space that is not covered by the detector units 310 of the first series. More specifically, the detector FOV 330 of the detector unit 310-6 is positioned to acquire image data from the working gap 454 between adjacent detector units 310-11 and 310-12, and the detector FOV 330 of the detector unit 310-5 is positioned to acquire image data from the working gap 454 between adjacent detector units 310-1 and 310-12. The detector FOV 330 of the detector unit 310-7 is positioned to acquire image data from a space that is adjacent to the detector FOV 330 of the detector unit 310-11.

Likewise, the detector units 310 of the first series in FIG. 7 have been positioned such that the corresponding detector FOVs 330 acquire image data from a space that is not covered by the detector units 310 of the second series. In particular, the detector FOV 330 of the detector unit 310-11 is positioned to acquire image data from the working gap 456 between adjacent detector units 310-6 and 310-7, and the detector FOV 330 of the detector unit 310-12 is positioned to acquire image data from the working gap 456 between adjacent detector units 310-5 and 310-6. The detector FOV 330 of the detector unit 310-1 is positioned to acquire image data from a space that is adjacent to the detector FOV 330 of the detector unit 310-5.

Unlike the imaging arrangement 350 (FIG. 5), the imaging arrangement 450 does not include overlapping regions among the detector FOVs 330. Moreover, the detector FOVs 330 are spaced apart from each other such that working voids 458 exist therebetween. In FIG. 7, a total of five working voids 458 exist and have different sizes. The working voids 458 represent spaces that separate the parallel lines that represent the detector FOVs 330. The size and number of working voids 458 is based on the configuration of the imaging arrangement. The working voids 458 do not necessarily cause gaps in the composite images. As described above, the openings in the collimators permit radioactive emissions to enter the collimators at non-orthogonal angles. As such, it is contemplated that photons emitted from the object within the working voids 458 may be detected by the detector units 310. Accordingly, composite images may be generated with data from the object within the working voids 458.

The detector FOVs form a collective FOV 460 that extends from one outer boundary 464 of the detector FOV of the detector unit 310-7 and an opposite outer boundary 466 of the detector FOV of the detector unit 310-1. Although the collective FOV 460 includes the working voids 458, the spaces occupied by the object in the working void 458 may be detected.

Figure 8:
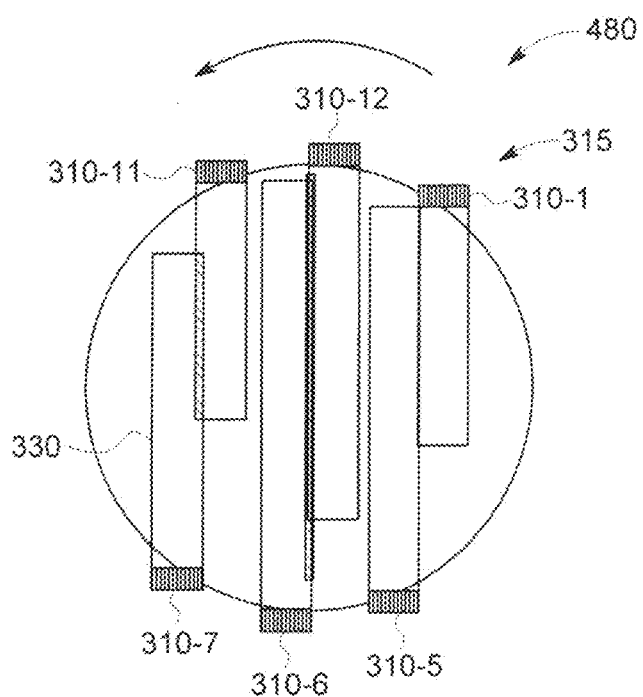
FIG. 8 illustrates the detector units of FIG. 4 after being moved to a different imaging arrangement in order to compensate or account for the working voids in FIG. 7.

In some embodiments, however, the working voids 458 may cause unwanted gaps in the resulting composite image or may cause delays or issues in generating the composite images. FIG. 8 illustrates an imaging arrangement 480 in which the working voids 458 of FIG. 7 are excessive in size. More specifically, in some embodiments, the set 315 of the detector units 310 may be rotated from one rotational position according to the imaging arrangement 450 to another rotational position according to the imaging arrangement 480 in order to detect image data from the working voids 458. In FIG. 8, the set 315 has been rotated CCW about 5°. The imaging arrangement 480 may acquire image data from the working void 458 (FIG. 7) that existed between the detector FOVs of the detector unit 310-12 and the detector unit 310-6. If necessary, the imaging arrangement 480 may acquire (a) image data from the working void 458 (FIG. 7) that existed between the detector FOVs 330 of the detector unit 310-1 and the detector unit 310-2 and/or (b) image data from the working void 458 (FIG. 7) that existed between the detector FOVs 330 of the detector unit 310-7 and the detector unit 310-11. However, it may not be necessary to obtain image data from these working voids 458 because the working voids 458 may be positioned outside of the ROI.

With respect to the working voids 458 that exists between the detector units 310-11 and 310-6 and between the detector units 310-12 and 310-5, the set 315 may be rotated in the CW direction to a new imaging arrangement (not shown). In some cases, however, it may not be necessary to acquire image data from more than two rotational positions. Accordingly, one or more persistence images of a designated anatomical plane may be obtained by slightly rotating the set 315 (e.g., by less than 20°) between different rotational positions and using image data from both rotational positions to generate the persistence images. As the position of the object is changed, the persistence images may be re-acquired. In such embodiments, the gantry may appear to be moving back and forth (or rocking back and forth) between two (or more) rotational positions to acquire the image data for the composite persistence images.

Although FIGS. 7 and 8 only illustrated the first and second series of detector units 310, it is also contemplated that the third and fourth series of detector units 310 may acquire image data in a similar manner. In some instances, image data for composite persistence images from two different anatomical planes may be simultaneously acquired by slightly rotating the set 315 between two different rotational position.

As described above, the image data acquired with different imaging arrangements may be acquired when the set of detector units are stationary. It is contemplated, however, that the image data may be acquired while the set of the detector units are moving. In such embodiments, the image data may be modified to compensate for the movement.

As described above, the image data acquired from the different series of detector units may be combined to form one or more composite persistence images. The composite persistence images may resemble planar images that are obtained by conventional NM imaging systems, such as H-mode images or L-mode images. Because the composite persistence images are based on interleaving detector FOVs, the image data may include overlapping region and/or regions with working voids. The image data also includes image data from detector units that face in opposite directions. Accordingly, it may be desirable to process the image data to give the approximate appearance of the ROI, which may be suitable for positioning the object within the bore.

To generate the composite persistence images, one or more image-processing algorithms may be executed. Each composite persistence image may be based on a grid of pixels. The grid may include pixels having dimensions that are less than the dimensions of the pixels from the image data, greater than the dimensions of the pixels from the image data, or equal to the dimensions of the pixels from the image data.

To generate composite images based on image data that includes an overlapping region, the image-processing algorithms may include discarding image data from the overlapping region. For example, if image data from an overlapping region is detected by two different detector units, the image data from one of the two detector units may be discarded and the image data from the other detector unit may be used to process (or generate) the composite persistence image. Alternatively, the image data from the overlapping region may be averaged and the averaged image data may be used to process the composite persistence image. The average may be an arithmetic average or a geometric average. As another option, the image data from an overlapping region that is used to process the composite persistence image may be selected based on the most intense pixel (MIP). For example, each pixel in an overlapping region could be assigned one of two intensity values, one from each detector unit. The most intense pixel (e.g., the pixel with the greatest intensity value) from either of the detector units may be selected as the pixel that will be used to process the composite persistence image. In addition to the above, if the pixel locations between two detector units that oppose each other do not exactly overlap, it may be desirable to interpolate the image data to a unified grid. A variety of interpolation algorithms may be used.

With respect to the working voids that exist between adjacent detector FOVs, if the working voids are relatively small (e.g., 0-5 pixels), the missing image data may be extrapolated by averaging the intensity values of the pixels that are adjacent to the working voids. For example, in simple one-dimensional (1D) extrapolation, the extrapolated value(s) may be the average of the two (or more) intensity values of the pixels that are located on either side of the working void in the same row. In weighted 1D extrapolation, the extrapolated value(s) may be the weighted average of the two (or more) values of the pixels that are located on either side of the working void in the same row, taking into account the distances from the centers of the known pixels to the location of the extrapolated pixel(s). Complex 1D extrapolation may include more processing steps. For example, a polynomial function may be fitted to the adjacent four pixels in the row (two on each side of the working void). The polynomial may be linear, cubic, or quadratic. The extrapolated value(s) of the missing pixel may be calculated. Alternatively, the extrapolation may include two-dimensional (2D) extrapolation, which may be similar to any of the 1D extrapolations described above, but include neighboring adjacent rows.

If the working voids are excessive, the set of detector units may be moved between different rotational positions or "rocked," as described above, to obtain image data from the different rotational positions. In such instances, it is possible that the image data may generate unbalanced images, because the working voids exist in some image data but not in other image data. This noise may be compensated for by using a sensitivity map for the different pixels in each detector unit. The sensitivity map may be based on the time spent at each rotational position. Alternatively, the set of detector units may be over-rotated (e.g., rotated beyond what is necessary) to account for the working voids so that the image data is more balanced.

It is possible that noise in the composite images will not be evenly distributed or that the images may not be balanced. For example, the composite images may have less quality than the images that are analyzed during diagnostic review. However, the quality of the composite images may be sufficient for determining a desired position of the object within the bore of the imaging system for subsequent diagnostic imaging. More specifically, it may not be necessary to obtain high quality persistence images in order to position the object within the bore.

It is understood that gamma photons are attenuated as the photons travel or propagate through material, such as the human body. Attenuation is greater for anatomical structures (e.g., organs) that are positioned at greater depths within the body, because the radiation must travel a greater distance through the body before reaching the detector. Thus, anatomical structures that are closer to one side of the patient may appear brighter in one detector but darker in another detector. By way of example, with respect to FIG. 5, if photons from an anatomical structure are detected by both of the detector units 310-1 and 310-5, but the anatomical structure is closer to the detector unit 310-1, then more photons will be detected by the detector unit 310-1. Thus, anatomical structures that are closer to one side of the patient will appear brighter for a first detector but darker for a second detector unit that is positioned further away from the anatomical structures.

Figure 17:
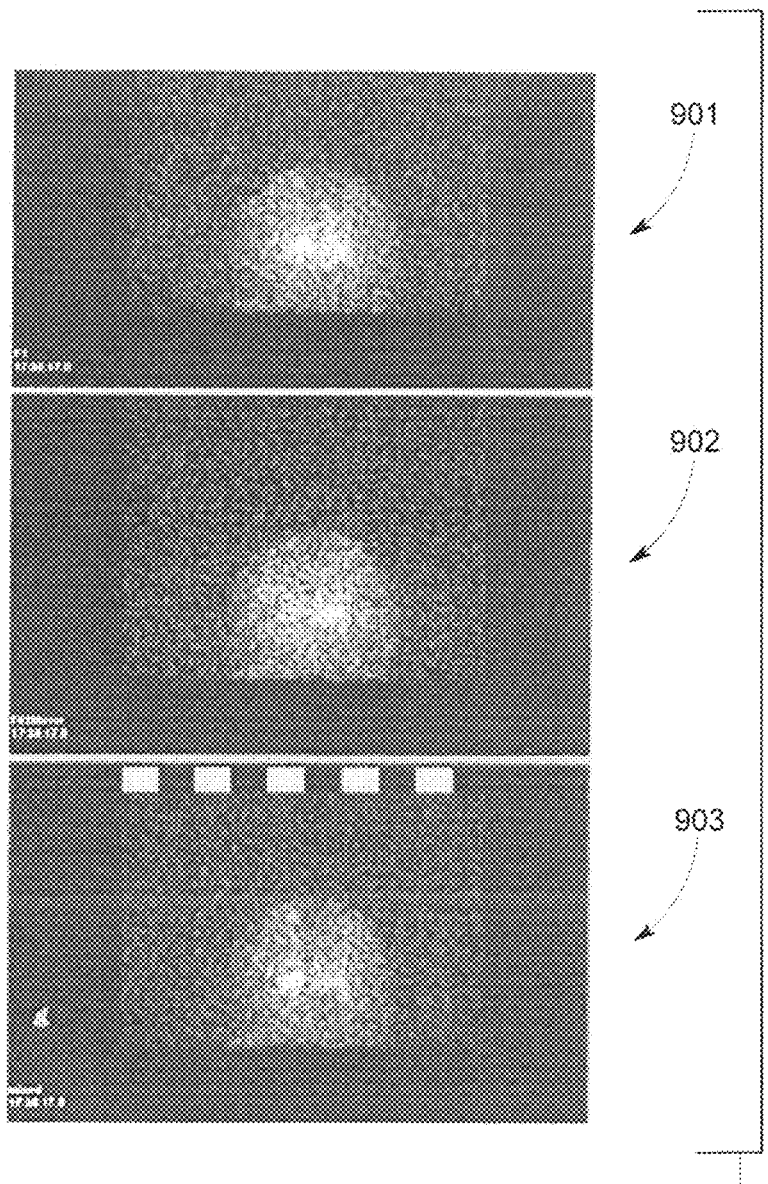
FIG. 17 illustrates first and second images from opposing detector units and a composite image that is based on the first and second images.
Figure 18:
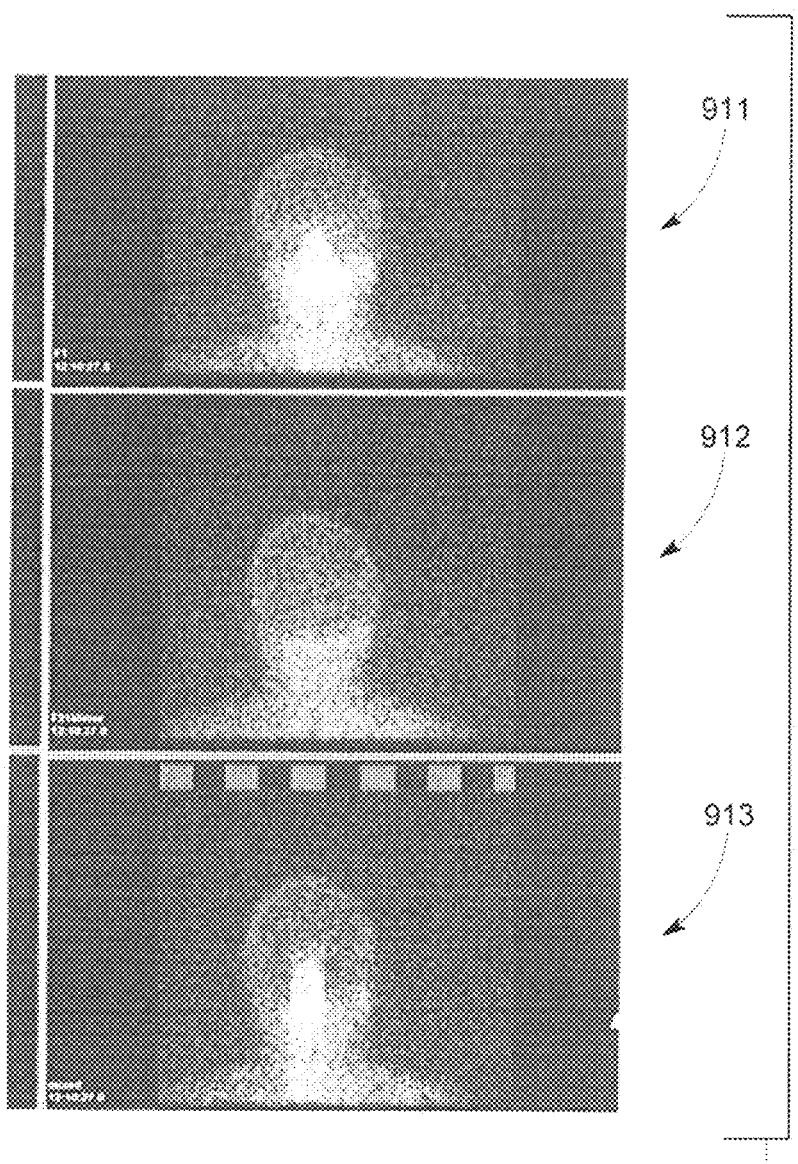
FIG. 18 illustrates first and second images from opposing detector units and a composite image that is based on the first and second images.

The amount of attenuation may also be based on the gamma energy of the photons. More specifically, photons having lower energy are more strongly attenuated than photons having higher energy. Accordingly, images from two opposing detector units may appear substantially dissimilar for lower energy photons. An example of lower energy photons are those that are radiated by Thallium. An example of higher energy photons are those radiated by Iodine. Thus, attenuation may be greater when Thallium is used for imaging. FIG. 17 illustrates top and bottom images 901, 902 and a composite image 903 that is based on the image data that formed the top and bottom images 901, 902. The top and bottom images 901, 902 were acquired from opposing detectors and from higher energy photons (e.g., Thallium). FIG. 18 illustrates top and bottom images 911, 912 and a composite image 913 that is based on the image data that formed the top and bottom images 911, 912. The top and bottom images 911, 912 were acquired from opposing detectors and from lower energy photons (e.g., Iodine). As shown in FIG. 17, the image is sufficient.

FIG. 18, however, includes artifacts that are caused by the attenuation of the photons and the detector units having FOVs that only partially overlap. In some cases, it is not necessary to take corrective action to improve the quality of the composite image. For instance, the composite image, even with artifacts, may be sufficient for positioning the patient. In other embodiments, however, one or more corrective actions may be taken to reduce the artifacts and/or enhance the quality of the composite image.

In one example, the gantry may be rotated as the photons are detected while each of the detector units is also selectively rotated. In other words, the gantry may be rotated and the detector units may be selectively rotated such that the detector FOV shifts laterally through ROI. In such embodiments, the gaps between adjacent detector units on one side of the patient may be "filled" by rotating the gantry and, consequently, the array of detector units and selectively rotating each of the detector units. This may be similar to an imaging process described in U.S. patent application Ser. No. 14/040,079 (Patent Publication No. 2015/0094573) ("the '079 Application"), which is incorporated herein by reference in its entirety. In particular, FIGS. 18-20 of the '079 Application illustrate a process for obtaining image data from one side of the patient. In the present application, the process may be applied to both sides of the patient in order to generate a persistence image used for positioning the patient.

In other embodiments, depending on the application, the detector units may be particularly configured for detecting photons from a designated isotope. In such instances, it may not be necessary to take corrective action for high energy isotopes, but it may be desirable to take corrective action for low energy isotopes. If the ROI is at a center of the body (e.g. deep lobes in the brain), it may not be necessary to take corrective action.

In other embodiments, the image data may be analyzed to determine whether the image data obtained from overlapping FOVs from opposing detector units is substantially different such that it is desirable to take corrective action. For example, the system may analyze the image data from the detector unit 310-1 and the image data from the detector unit 310-5, which were required from overlapping FOVs. If the image data from the detector units is substantially different, then the system may take corrective action. If the image data from the detector units is not substantially different, however, then the system may determine that it is not necessary to take corrective action. The image data from opposing detectors may be substantially different if the image data satisfies one or more designated conditions. For example, if the "adjacent strips" corresponding to opposing detectors are statistically different in brightness by more than a designated percentage (e.g. 20%), then the system may take corrective action, such as one or more of the corrective actions described herein. If the brightness is not significantly different, then the system may not take corrective action. Based on the above, the system may determine to acquire panoramic image data for persistence images as described below.

Figure 9A:
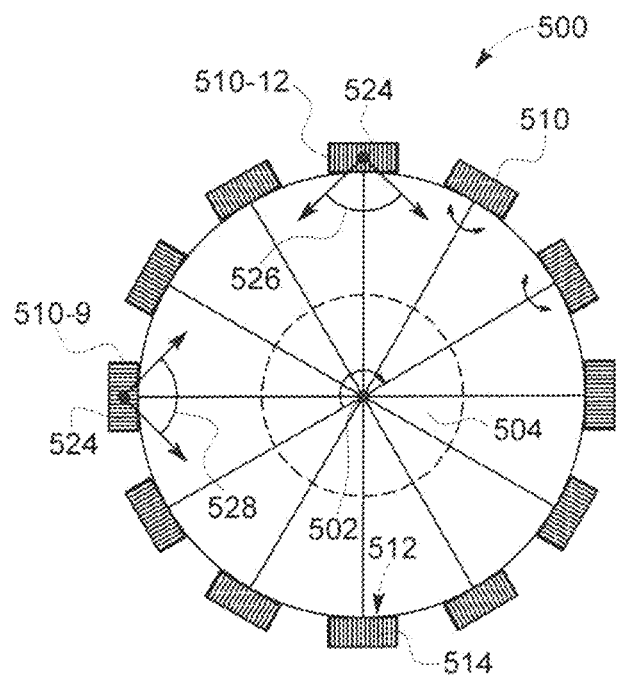
FIG. 9A illustrates an imaging arrangement of detector units in accordance with an embodiment.

FIG. 9A illustrates an imaging arrangement 500 of an imaging system (not shown) formed in accordance with an embodiment. The imaging system may be similar or identical to the imaging system 100 (FIG. 1). As shown, a central longitudinal axis 502 extends into and out of the page. The longitudinal axis 502 may extend lengthwise through a center of a bore 504 (indicated by dashed line) of a gantry (not shown). The imaging arrangement 500 includes a plurality of detector units 510. Each of the detector units 510 includes a detection or acquisition surface 512 and a collimator 514.

Embodiments set forth herein include imaging arrangements in which a select number of the detector units are configured to acquire panoramic image data of the object. Based on the panoramic image data, a technician (or automated system) may position the object within the bore. For example, the imaging arrangement 500 includes a first detector unit 510-12 and a second detector unit 510-9. Optionally, the first and second detector units 510-12, 510-9 may have substantially perpendicular positions with respect to each other. For example, the first detector unit 510-12 has a 12 o'clock (or 0°) position with respect to the longitudinal axis 502 and the second detector unit 510-9 has a 9 o'clock (or 270°) with respect to the longitudinal axis 502. Accordingly, the first and second detector units 510-12 and 510-9 have substantially perpendicular positions with respect to each other and the longitudinal axis 502.

Due to the different positions with respect to the longitudinal axis 502, the first and second detector units 510-12, 510-9 may obtain image data along different anatomical planes, although the resulting composite persistence image may not resemble a planar image. For example, the first detector unit 510-12 may acquire a coronal panoramic image, and the second detector unit 510-9 may acquire a sagittal panoramic image. Such embodiments may be particularly suitable for persistence imaging of ROIs having a smaller volumes, such as ROIs that include the head or brain.

Each of the first and second detector units 510-12, 510-9 is configured to be rotated about a respective unit axis 524 and acquire image data as the first and second detector units 510-12, 510-9 are detected. For example, the first and second detector units 510-12, 510-9 may be incrementally rotated within sweep ranges 526, 528, respectively. One or more projections may be obtained at each rotational position. This may be similarly to a step-and-shoot process. For instance, the first detector unit 510-12 may be rotated from one rotational position to a subsequent rotational position. The rotational positions may differ by a designated angle, such as 6.7°. When the first detector unit 510-12 is stationary at a designated rotational position, the first detector unit 510-12 may acquire image data that is processed into a corresponding projection. The first detector unit 510-12 may then be rotated to the next rotational position. The next rotational position may differ from the previous rotational position by the same angle (e.g., 6.7°) or by a different angle. The designated angle or angles may be based on the size of the ROI and a number of desired projections. For example, the number of desired projections may be a number that is suitable for determining whether the ROI is properly positioned. Accordingly, a series or set of projections may be obtained that includes at least one projection from each rotational position. As an example, each of the rotational positions may differ from the prior or subsequent rotational position by 6.7°. A total of 14 projections may be acquired. In this example, the sweep range is 94°. The second detector unit 510-9 may be operated in a similar or identical manner to acquire a series of projections at different rotational positions. Thus, embodiments may acquire one or more series or sets of projections. In FIG. 9A, the detector unit 510-12 obtains a coronal panoramic set of projections, and the detector unit 510-9 acquires a sagittal panoramic set.

Figure 9B:
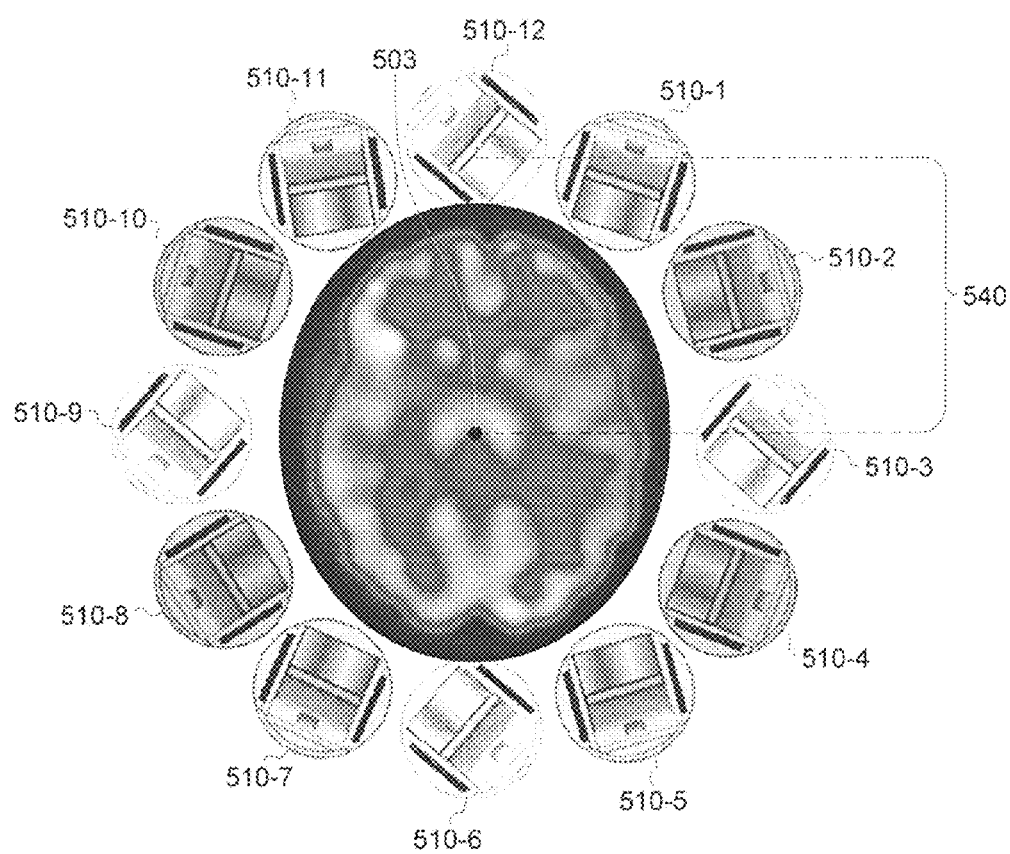
FIG. 9B illustrates the imaging arrangement of FIG. 9A in which the detector units have been positioned for brain persistence imaging.

In some embodiments, the composite persistence image is formed from the series of projections acquired by a single detector unit. In other embodiments, the composite persistence image may be based on image data acquired from multiple detector units. FIG. 9B illustrates an example in which each persistence image is based on data from multiple detector units. In FIG. 9B, the detector units 510-1 through 510-12 have been positioned around a head (or brain) for persistence imaging. For example, the radial positions of the detector units 510-1 through 510-12 relative to a center axis 503 through the patient have been decreased so that the detector units 510-1 through 510-12 are more closely positioned with respect to the head and each other. The center axis 503 may or may not be aligned with the longitudinal axis 502. By way of example, a radial distance 540 between the detection or acquisition surface of the detector unit 510-12 and the center axis 503 through the patient may be about 17 cm. The separation distances between adjacent detector units have decreased and are less than, for example, the separation distances between the detector units 510-1 through 510-12 in FIG. 9A, such as when a chest is being imaged.

In FIG. 9B, a single composite image (e.g., coronal persistence image) may be based on image data from detector units 510-1, 510-5, 510-7, and 510-11. Another composite image (e.g., the sagittal persistence image) may be based on image data from detector units 510-2, 510-4, 510-8, and 510-10. The detector units 510-1, 510-5, 510-7, and 510-11 form a first operative set, and the detector units 510-2, 510-4, 510-8, and 510-10 form a second operative set. In the illustrated embodiment, each of the detector units in the first operative set is positioned substantially opposite at least one other detector unit in the first operative set (e.g., detector units 510-5 and 510-11 are substantially opposite each other). Each of the detector units in the second operative set is positioned substantially opposite at least one other detector unit in the second operative set (e.g., detector units 510-2 and 510-8 are substantially opposite each other). In some embodiments, each of the detector units in the first operative set may be substantially perpendicular to at least one other detector unit in the second operative set and/or vice versa (e.g., detector unit 510-1 of the first operative set and detector unit 510-4 of the second operative set are substantially opposite each other). Moreover, the first and second operative sets may be configured to acquire data for obtaining persistence images along perpendicular planes. For example, the first operative set may acquire data for generating a coronal persistence image, and the second operative set may acquire data for generating a sagittal persistence image. The coronal and sagittal persistence images represent persistence images that are acquired along perpendicular planes.

Each of the detector units in the first and second operative sets may simultaneously or concurrently rotate about the respective unit axis within the sweep range. Thus, in the illustrated embodiment, all eight detector units may rotate simultaneously or concurrently. As used herein, the term "concurrently" means at least partially overlapping. In this example, each of the detector units 510-1, 510-5, 510-7, and 510-11 of the first operative set concurrently rotates in a step-like manner to acquire a plurality of projections. Each of the detector units 510-2, 510-4, 510-8, and 510-10 of the second operative set concurrently rotates in a step-like manner to acquire a plurality of projections. As described above, each of the select detector units 510 may be rotated about a sweep range and a series of projections may be acquired at different rotational positions. The amount of rotation between different steps or rotational positions may be, for example, the inverse tangent of the size of the volume-of-interest and the radial distance 540 between the acquisition surface and the center axis. For example, if the size of the volume-of-interest is 2 cm and the radial distance is 17 cm, then $\tan^{-1}$ (2 cm/17 cm)=6.7°. In this example, each of the rotational positions may differ from the prior or subsequent rotational position by 6.7°. A total of 14 projections may be acquired. In this example, the sweep range is 94°. It should be noted, however, that the calculations for each detector unit may be different based on, for example, the radial position of the corresponding detector unit.

In some cases, embodiments that use multiple detector units for a single composite image may better locate a ROI having multiple anatomical structures that are desired to be image. For example, the separate kidneys of a patient may be more easily identified using composite images that are generated from image data of multiple detector units. Such embodiments may also decrease the time necessary to positioned the patient by acquiring the data for the persistence images more quickly.

Figure 10:
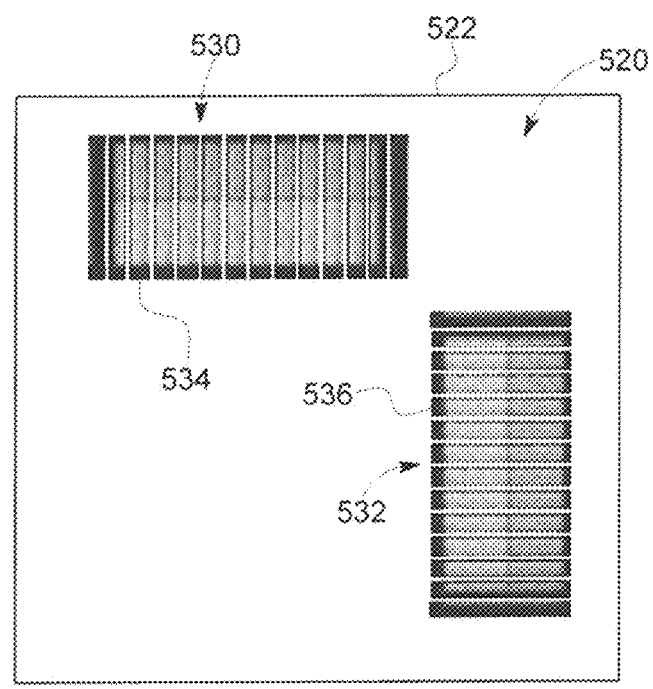
FIG. 10 illustrates a screen that may be displayed to a user that includes a composite persistence image obtained by the imaging arrangement in FIG. 9A.

FIG. 10 illustrates a user screen 520 that may be displayed to user on a display 522. As shown, the user screen 520 includes a first composite persistence image 530 (e.g., coronal composite image) and a second composite persistence image 532 (e.g., sagittal composite image). Unlike the composite persistence images generated by embodiments in accordance with FIGS. 4-8, which resemble planar images, the composite persistence images 530, 532 include series of projections 534, 536, respectively. The projections of each series are positioned side-by-side. The relative location of each projection is based on the rotational position of the detector unit when the image data for the projection was acquired. A user (e.g., technician) may view the projections 534, 536 to determine a lateral position of the object and an elevation of the object. Either of the composite images 530, 532 may be used to determine a longitudinal position of the object.

Figure 11:
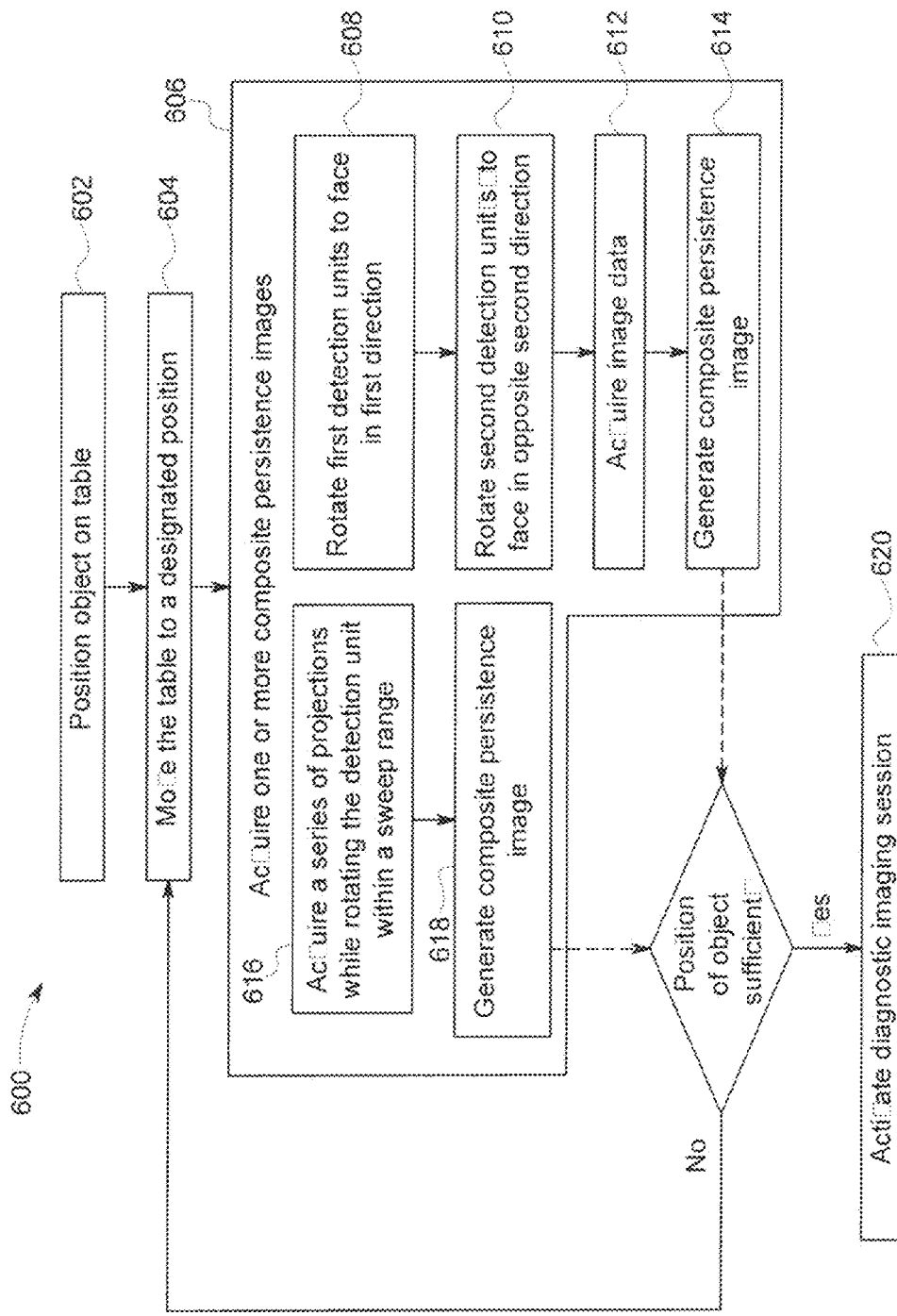
FIG. 11 shows a flowchart of a method in accordance with an embodiment.

FIG. 11 shows a flowchart of a method 600 in accordance with an embodiment. The method 600 may include, for example, positioning an object within a bore of an NM imaging system using persistence images obtained by the NM imaging system. The method 600 may be performed, at least in part, using the NM imaging system 100. The method 600 may also include obtaining higher quality diagnostic images of an object after the object has been positioned using the persistence images. One or more steps of the method 600 may be performed by one or more processors of the NM imaging system. One or more steps of the method 600 may also be based on user inputs. For example, a technician may use a remote control unit (RCU) that controls movement of the table. The technician may move the table in response to the persistence images acquired by the NM imaging system.

The method 600 may include positioning, at 602, an object onto a table within the bore of the NM imaging system. Optionally, the method 600 may include moving the table, at 604, to a designated position within the bore. At 606, one or more composite persistence images may be acquired. One or more processes may be executed, in an iterative manner, to acquire the composite persistence images.

For example, the composite persistence images may be acquired by rotating, at 608, a plurality of first detector units to face in a common first direction that is generally toward the bore. A working gap may exist between detector FOVs of the respective first detector units. At 610, one or more second detector units may be rotated to face in a second direction that is opposite the first direction. The detector FOV of the second detector unit may include the working gap that exists between adjacent first detector units. At 612, image data may be acquired by the first detector units and the second detector unit. At 614, a composite persistence image may be generated based on the image data.

The method 600 may also include repeating the step of moving the table, at 604 in order to adjust the position of the table within the bore based on the composite persistence image. For example, the composite persistence image may be displayed on a display of the NM imaging system. The user may review the composite persistence image and, based on the position of the ROI in the composite persistence image, move the table, at 604, to a different position. In some embodiments, the NM imaging system may analyze the composite persistence image and, based on this analysis, automatically move the table at 604. In some embodiments, the NM imaging system may analyze the composite persistence image and, based on this analysis, display a suggestion to the user for moving the table. After moving the table, the process may again acquire, at 606, one or more composite images.

After moving the table, at 604, one or more times, the user or the system may determine that the position of the object within the bore is sufficient. At this time, the user or the system may activate, at 620, a diagnostic imaging session. The diagnostic imaging session may use the same detector units that acquired the persistence images. However, the image data acquired by the detector units may be used to generate higher quality images for diagnosis.

Optionally, the method 600 may generate one or more composite images based on panoramic data. For example, the acquisition, at 606, may include rotating, at 616, one or more detector units about a unit axis within a respective sweep range while acquiring a series of image projections. The projections may be positioned side-by-side and displayed to the user as a composite image. The method 600 may include repeating the step of moving the table, at 604, in order to adjust the position of the table within the bore based on the composite image formed from panoramic data.

Figure 12:
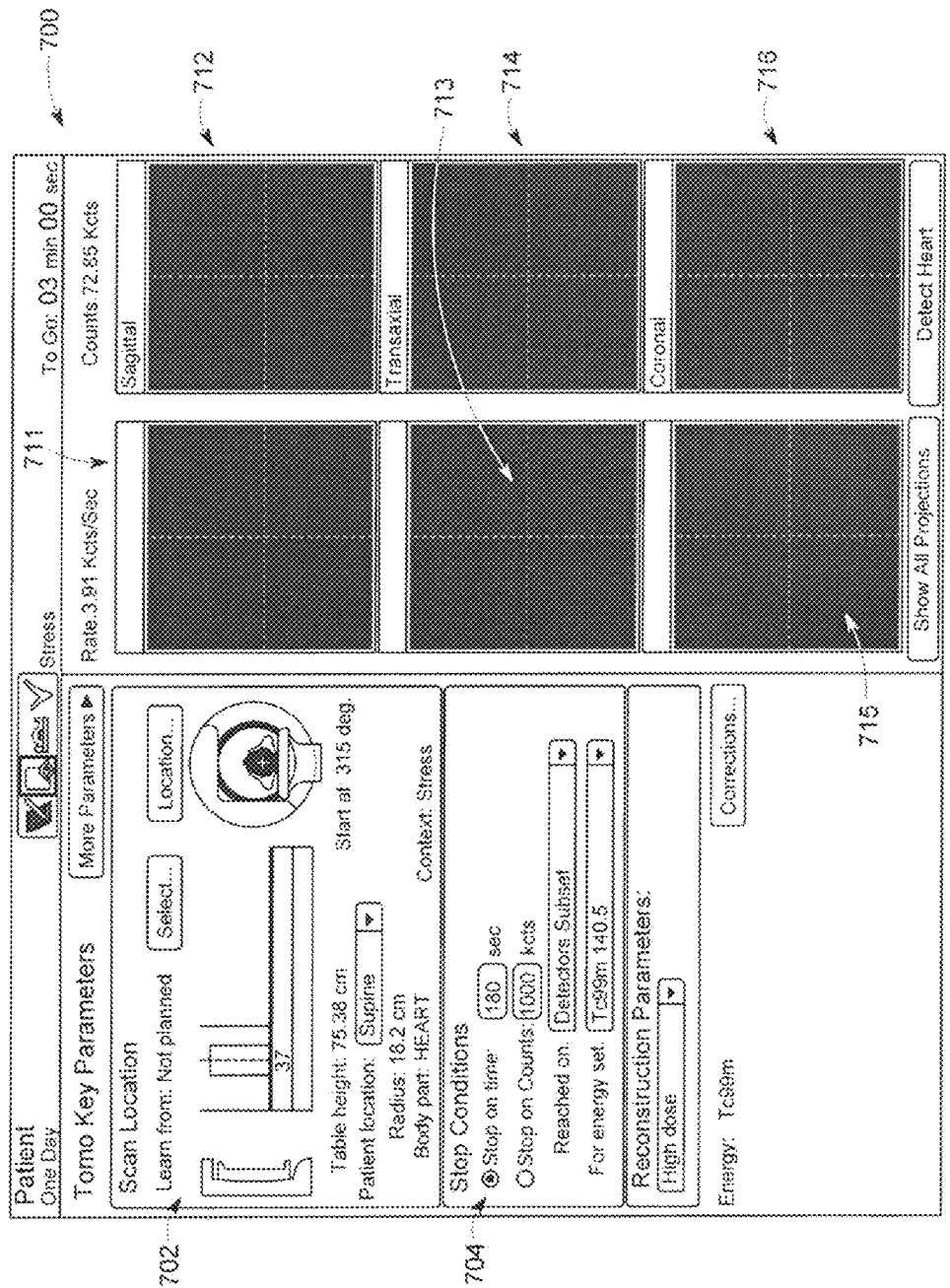
FIG. 12 illustrates a workflow screen that may be displayed to a user of an NM imaging system in accordance with an embodiment.

FIGS. 12-16 illustrate different workflow screens and graphical elements that may be presented to a user during a position-determining operation and subsequent imaging session. FIG. 12 shows a workflow screen 700 that displays information to the user. The workflow screen 700 may be presented on the display 168 (FIG. 1). The user may use the user input device 166 (FIG. 1) to enter user inputs. The user inputs may be used to control, for example, the detector units of the NM imaging system during persistence imaging and/or during diagnostic imaging. The user input device 166 may be any device capable of communicating the inputs to the system. For example, the user input device 166 may include a keyboard, mouse, tracking pad, and/or a touch-sensitive screen. In some embodiments, the user input device 166 may include a processing unit that detects audio inputs from the user and processes the audio inputs into user inputs.

The workflow screen 700 includes a plurality of user-selectable elements and/or data fields for entering user inputs. For example, the workflow screen 700 includes a positioning frame or field 702 for entering information about the scan of interest. The workflow screen 700 also includes a scan-duration frame or field 704 for entering information regarding a duration of the scan. For example, a user may instruct the system to stop scanning based on time (e.g., number of seconds), based on a total number of photon counts (e.g., kilocounts (kcts)), whichever condition occurs first, or whenever both conditions are satisfied.

The workflow screen 700 also includes a plurality of image fields or frames 711-716. Each of the image fields 711-716 is configured to display an image, such as a persistence image or an image slice, to the user. The image fields 711-716 may correspond to different anatomical planes. For example, in the illustrated embodiment, the image fields 711, 712 correspond to a sagittal plane, the image fields 713, 714 correspond to a trans-axial plane, and the image fields 715, 716 correspond to a coronal plane.

Figure 13:
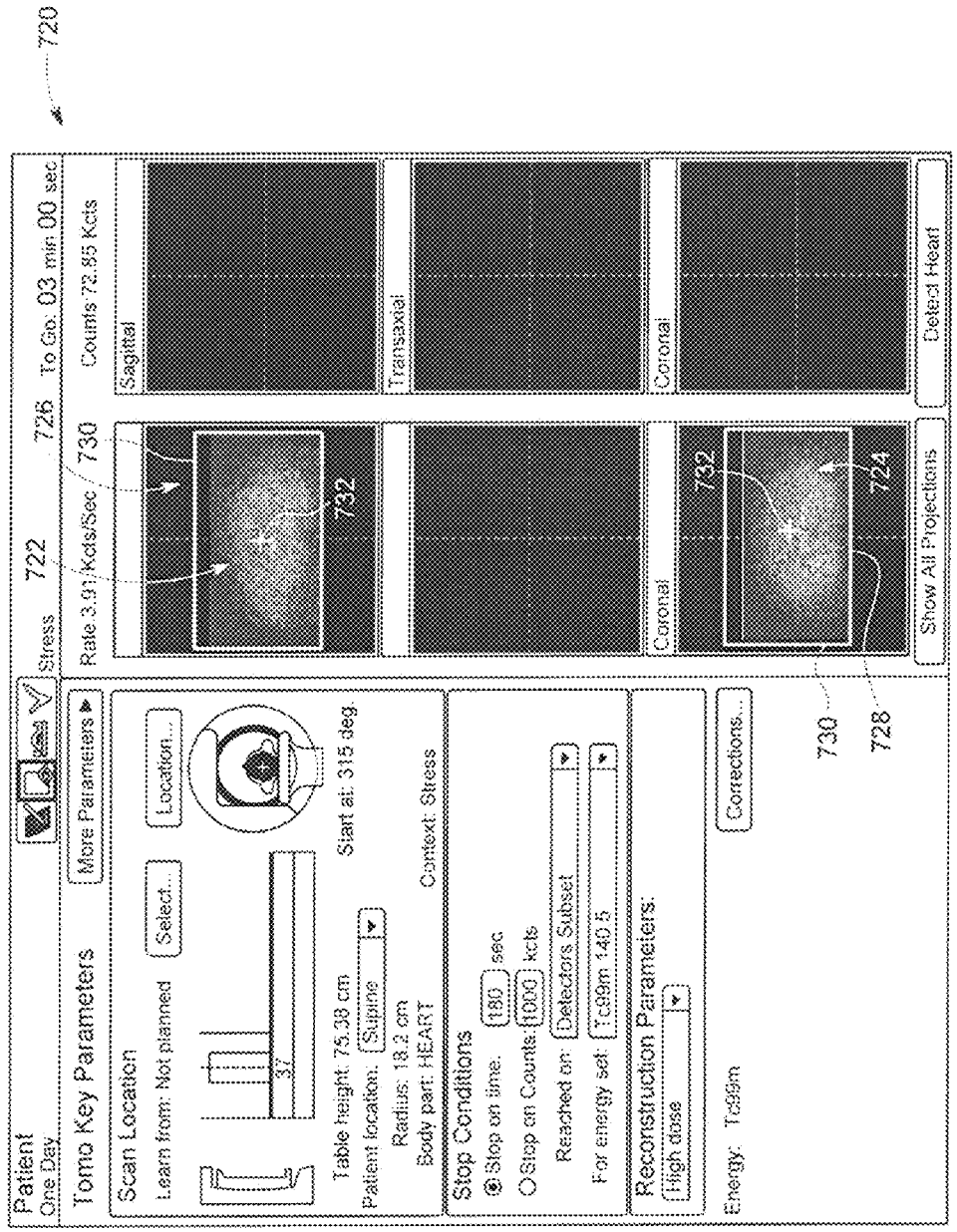
FIG. 13 illustrates a workflow screen displaying persistence images of two different anatomical planes.

FIG. 13 illustrates a workflow screen 720 after image data has been acquired and persistence images 722, 724 have been displayed. The workflow screen 720 includes similar or identical frames or fields from the workflow screen 700 (FIG. 12). In some embodiments, the system may enable a user to selectively control the FOV of the imaging system. For example, the system may display field-control elements 726, 728 over the persistence images 722, 724, respectively. The field-control elements 726, 728 are graphical elements that are sized and shaped based on the current or present FOV of the imaging system. As shown, the field-control elements 726, 728 include rectangular boxes that indicate a field perimeter 730 (e.g., a perimeter of the FOV for the corresponding anatomical plane) and crosshairs that indicate a field center 732 (e.g., a center of the FOV for the corresponding anatomical plane).

The user may enter user inputs for moving the field perimeter 730 with respect to the persistence image and/or re-shaping the field perimeter 730 with respect to the persistence image. In response to these user inputs, the system may automatically adjust imaging parameters of the system, such as the positions of the table and/or positions of the detector units. For example, the workflow screen 720 may enable the user to identify the ROI to be imaged and move the field perimeter 730 such that the field perimeter 730 surrounds or encompasses the desired ROI. For example, the user may re-position the field perimeter 730 by locating the field center 732 at a center of the desired ROI. The field perimeter 730 may be moved by selecting the field perimeter with a mouse and/or by using arrow keys of keyboard. However, these are only examples and other methods of moving the field perimeter may be performed. For example, the field perimeter 730 may be moved by the user touching the display (e.g., a touch-sensitive display) and moving the field perimeter 730 and/or by voice command.

In addition to moving the field perimeter 730, the user may enter user inputs for re-shaping the field perimeter 730. For example, the user may enter values for defining one or more dimensions that define the field perimeter 730. The dimensions may be, for example, a width, height, length, diameter (or other dimension) of the field perimeter 730. In some cases, the user may move the lines that define the designated dimension relative to the persistence image.

After re-shaping the field perimeter 730, the system may automatically determine values for the dimensions. In response to moving the field perimeter 730 and/or re-shaping the field perimeter 730, the system may automatically re-position the table and/or detector units. For example, the system may selectively move one or more of the detector units closer to or away from the ROI. Alternatively or in addition to changing the radial positions of the detector units, the system may selectively move one or more of the detector units to a different circumferential position. Moreover, the system may selectively move (e.g., selectively rotate) the set of detector units as a group. The detector units may be automatically moved after the user has moved or otherwise modified the field-control units. Alternatively, after the user has moved or otherwise modified the field-control units, the system may prompt or query the user to confirm that the system is permitted to move the detector units. After re-positioning the detector units, the system may then acquire image data for new persistence images. When the user is satisfied with the position of the patient and the parameters of the imaging protocol, the user may initiate a diagnostic imaging session.

Figure 14:
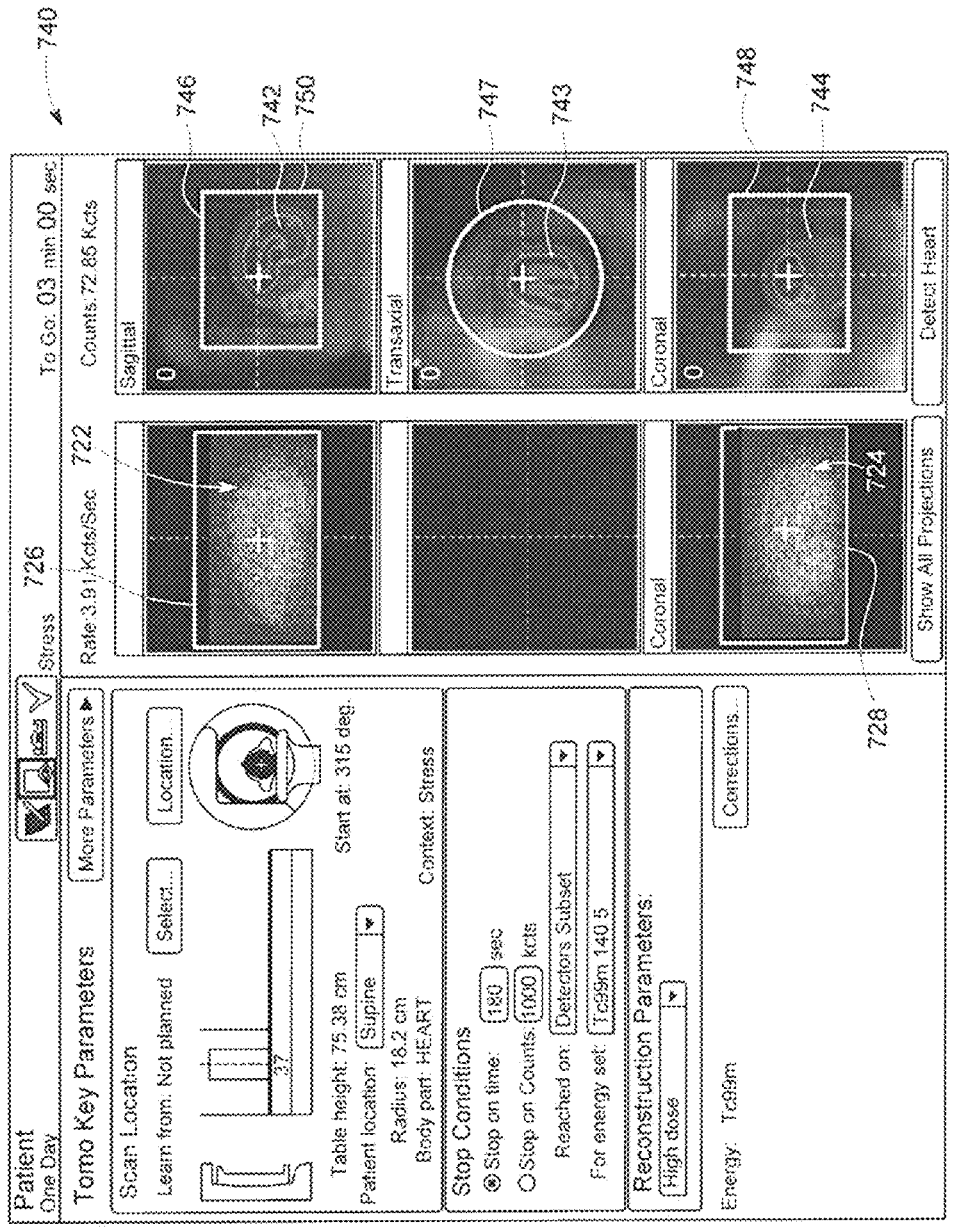
FIG. 14 illustrates a workflow screen displaying persistence images of two different anatomical planes and slices from three-dimensional (3D) imaging data.

FIG. 14 illustrates a workflow screen 740 for displaying the persistence images 722, 724 of the two different anatomical planes and slices 742, 743, 744 from three-dimensional (3D) image data. In some embodiments, the imaging system may also acquire 3D image data using, for example, the panoramic imaging methods described above or data from other imaging modalities. It is contemplated that the 3D image data may be obtained in other manners. The system may process the 3D image data and display slices of the 3D image data that correspond to the anatomical planes of the persistence images 722, 724. The system may also display field-control elements 746, 747, and 748 over the slices 742, 743, and 744, respectively. As described above with respect to the field-control elements 726, 728, the user may modify or adjust a field perimeter 750 with respect to the slices in order to re-position the patient and/or control the imaging protocol. The system may then acquire image data for new persistence images. When the user is satisfied with the position of the patient and the parameters of the imaging protocol, the user may initiate a diagnostic imaging session.

Figure 15:
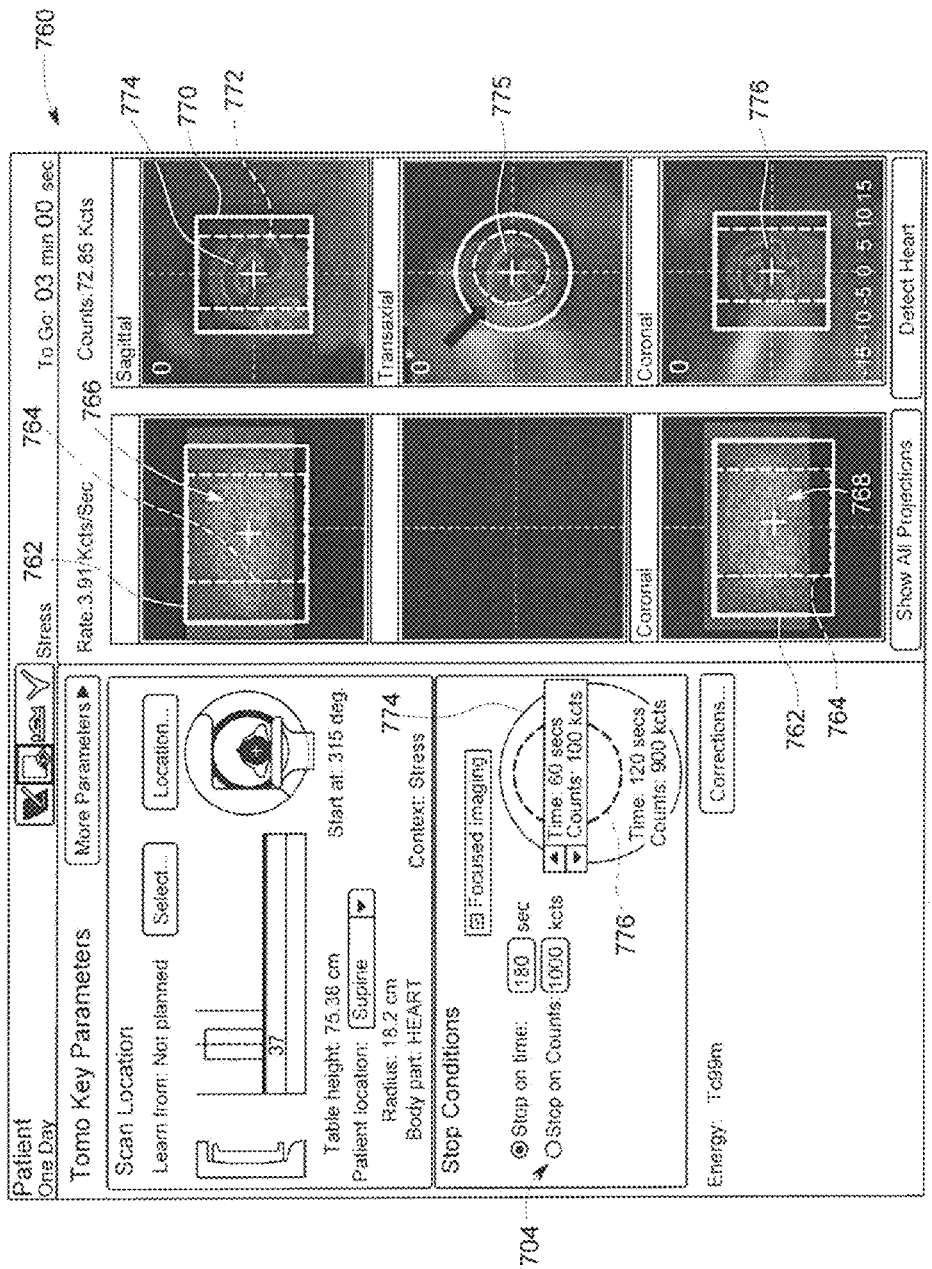
FIG. 15 illustrates a workflow screen displaying images with overlying graphical elements for designating regions for focused imaging.

FIG. 15 illustrates a workflow screen 760 displaying multiple field-control elements 762, 764 over respective persistence images 766, 768 and multiple field-control elements 770, 772 over respective slices 774, 775, 776 from the 3D image data. In some embodiments, the system may enable the user to control the detector units for a focused-imaging protocol. During a focused-imaging protocol, the detector units may acquire image data from a first FOV and then a second FOV. In some embodiments, the second FOV is within the first FOV. In other words, the first FOV is larger than the second FOV. Image data acquired from the first FOV may then be enhanced using image data from the second FOV. As such, images obtained may have a higher quality within the second FOV while also conveying information regarding the area that surrounds the second FOV and is defined by the first FOV. To this end, each of the field-control elements 762, 764 and the field-control elements 770, 772 may be selectively controlled by the user to identify the first FOV and the second FOV. For example, the field-control elements may include field perimeters that may be moved or modified as described above with respect to the field perimeters 730.

For a focused-imaging protocol, the user may selectively control (a) the sizes and shapes of the regions that will be imaged and (b) a duration in which each of the regions will be imaged. For example, after identifying the sizes and shapes of the regions to be imaged by adjusting the field perimeters, the user may enter user inputs regarding the time duration. As shown, the user may select or enter user inputs into the scan-duration field 704. The scan-duration field 704 includes a first FOV representation 774 and a second FOV representation 776. The user may select either of the FOV representations 774, 776 and then enter user inputs regarding the duration for the respective FOV. The first and second FOV representations 774, 776 are illustrated as ovals or circles in the illustrated embodiment. The first and second FOV representations 774, 776 may have other shapes in other embodiments. For example, the first and second FOV representations 774, 776 may be identical to the corresponding field-control elements.

As an example of a focused-imaging protocol, the user may select the first FOV representation 774 and then enter inputs that instruct the system to stop acquiring image data after a designated time period has elapsed or after a total number of photons have been detected. In some cases, the user may instruct the system to stop acquiring image data when either of these conditions has been satisfied or when both conditions have been satisfied. Using the example shown in FIG. 15, the system may acquire image data from the first FOV for 120 seconds and then acquire more image data from the second FOV for an additional 60 seconds. The resulting diagnostic images may have a higher quality for portions within the second FOV. Nonetheless, useful information regarding the area that surrounds the second FOV and is defined by the first FOV may be determined from the diagnostic images.

Although the illustrated embodiment shows two FOVs in which one of the FOVs is within another FOV, it is contemplated that the two FOVs in other embodiments may be separate (e.g., non-overlapping or only sharing a border). It is also contemplated that image data from three FOVs may be acquired. For example, the first FOV may encompass the second and third FOVs and the second and third FOVs may be separate within the first FOV. Such configurations may be useful for imaging kidneys of a patient.

Figure 16:
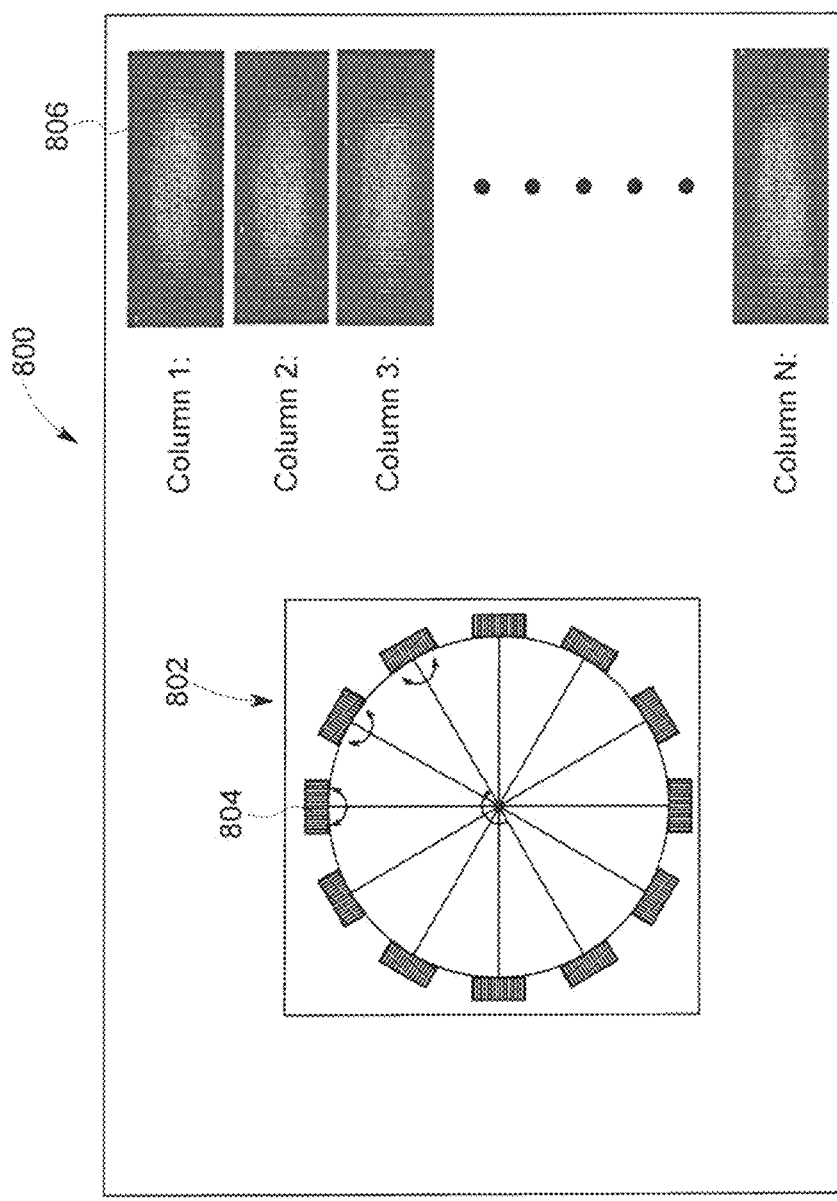
FIG. 16 illustrates a workflow screen that may be displayed to a user of an NM imaging system in accordance with an embodiment.

FIG. 16 illustrates a workflow screen 800 that may be displayed to a user of an NM imaging system in accordance with an embodiment. The workflow screen 800 illustrates a representation 802 of a detector arrangement of the imaging system. The representation 802 of the detector arrangement includes a representation 804 of each of the detector units in the detector arrangement. Embodiments set forth herein may enable a user to select which detector units to use during persistence imaging or during the diagnostic imaging. For example, in FIG. 16, the user may select the representations 804 that correspond to the detector units 12 and 9 for obtaining panoramic image data. The image data may be processed to generate composite persistence images 806 that may be displayed within the workflow screen 800.

In some embodiments, the user may be permitted to select the detector units to be used for persistence imaging to generate planar persistence images (or pseudo-planar persistence images). For example, the user may select the representations 804 of the detector units 11, 12, and 1 on one side of the object and the representations 804 of the detector units 5, 6, and 7 on the opposite side of the object. Optionally, the user may be capable of selecting the relative positions of the detector units for persistence imaging.

Figure 19:
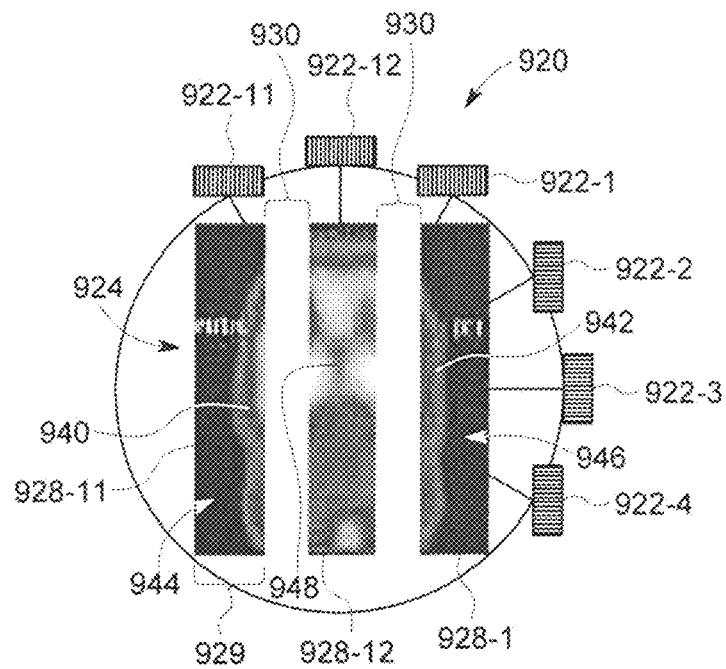
FIG. 19 illustrates an imaging arrangement of detector units in accordance with an embodiment and shows a first persistence image.
Figure 20:
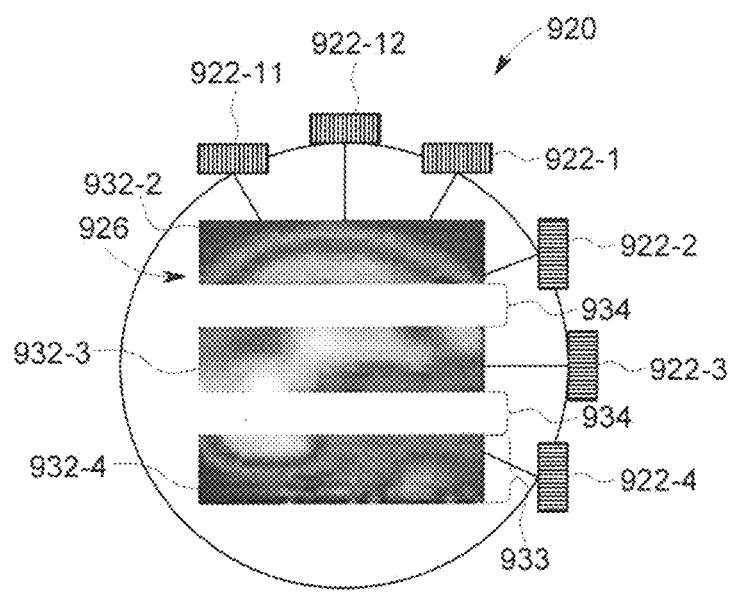
FIG. 20 illustrates the imaging arrangement of FIG. 19 with a second persistence image.

FIGS. 19 and 20 illustrate an imaging arrangement 920 in which a plurality of detector units 922-11, 922-12, and 922-1 are configured to acquire image data for a first persistence image 924 (FIG. 19) of the ROI and a plurality of detector units 922-2, 922-3, and 922-4 are configured to acquire image data for a second persistence image 926 (FIG. 2) of the ROI. Each of the detector units 922-11, 922-12, and 922-1 faces in a common first direction, and each of the detector units 922-2, 922-3, and 922-4 faces in a common second direction. The detector units 922-11, 922-12, and 922-1 are separated by corresponding separation distances, and each of the detector units 922-2, 922-3, and 922-4 1 are separated by corresponding separation distances. The separation distances may be the same or may be different.

For illustrative purposes, the first and second persistence images 924, 926 are shown in FIGS. 19 and 20, respectively. In the illustrated embodiment, the first persistence image 924 is a coronal persistence image of the ROI. The second persistence image 926 is a sagittal persistence image of the ROI. The ROI is a patient's head or brain in the illustrated embodiment. The first and second persistence images 924, 926 may be displayed to a user during a position-determining operation, which may include similar or identical steps as descried with respect to the method 600 (FIG. 11). The display may be similar to the display 168 (FIG. 1).

The first and second persistence images 924, 926, however, do not provide complete or continuous images of the ROI. Instead, the first and second persistence images 924, 926 are fractured or incomplete images that include image swaths (or image sections) and working gaps between the image swaths. More specifically, as shown in FIG. 19, the first persistence image 924 includes a plurality of image swaths 928-11, 928-12, and 928-1 that are separated by working gaps 930. The image swaths 928-11, 928-12, and 928-1 are formed from image data acquired by the respective detector units 922-11, 922-12, and 922-1. More specifically, the image swaths 928-11, 928-12, and 928-1 may correspond to the detector FOVs. The image swaths 928-11, 928-12, and 928-1 have a width 929. As shown in FIG. 20, the second persistence image 926 includes a plurality of image swaths 932-2, 932-3, and 932-4 that are separated by working gaps 934. The image swaths 932-2, 932-3, and 932-4 are formed from image data acquired by the respective detector units 922-2, 922-3, and 922-4. More specifically, the image swaths 932-2, 932-3, and 932-4 may correspond to the detector FOVs. The image swaths 932-2, 932-3, and 932-4 have a width 933.

During the position-determining operation, at least one of the first or second persistence images 924, 926 may be displayed to the user. For example, the first and second persistence images 924, 926 may include only the corresponding image swaths or may include the corresponding image swaths separated by the corresponding working gaps. In other embodiments, the first or second persistence images 924, 926 may include only the image swaths. The image swaths may be visually separated or otherwise differentiated so that the user may understand that the image swaths are from different detector units. For example, a separator line (not shown) may divide adjacent image swaths when the persistence image is displayed to the user.

Although the first and second persistence images 924, 926 are incomplete, the user may be able to position the patient (or object) based on the information provided by the first and second persistence images 924, 926. For example, the image swaths 928-11 and 928-1 include anatomical portions 940, 942, respectively, and open spaces 944, 946, respectively. The user may be able to determine that the anatomical portions 940, 942 include outer boundaries of the ROI based on the open spaces 944, 946. In other words, the anatomical portions 940, 942 extend along only a portion of the width 929 of the image swath. The image swath 928-12 includes an anatomical portion 948 that extends through an entire width 929 of the image swath 928-12.

As such, the user may re-position the ROI so that the detector units 922-11 and 922-1 are aligned with edges or boundaries of the ROI and so that the detector unit 922-12 is aligned with a central region of the ROI. In some embodiments, when the detector unit 922-12 is equally spaced apart from the detector units 922-11 and 922-1, the user may determine that the detector unit 922-12 is positioned to image a center of the ROI. Although the above was described with specific reference to the first persistence image 924, the user may re-position the ROI using the second persistence image 926 in a similar manner. Thus, in some embodiments, a user may use incomplete persistence images to position the patient relative to the detector units for subsequent diagnostic imaging. As described above with respect to other embodiments, the first and second persistence images 924, 926 may be acquired concurrently or simultaneously.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a processor or a processing unit includes processing circuitry configured to perform one or more tasks, functions, or steps, such as those described herein. For instance, the processor may be a logic-based device that performs operations based on instructions stored on a tangible and non-transitory computer readable medium, such as memory. It may be noted that a "processor," as used herein, is not intended to necessarily be limited to a single processor or single logic-based device. For example, the processor may include a single processor (e.g., having one or more cores), multiple discrete processors, one or more application specific integrated circuits (ASICs), and/or one or more field programmable gate arrays (FPGAs). In some embodiments, the processor is an off-the-shelf device that is appropriately programmed or instructed to perform operations, such as the algorithms described herein.

The processor may also be a hard-wired device (e.g., electronic circuitry) that performs the operations based on hard-wired logic that is configured to perform the algorithms described herein. Accordingly, the processor may include one or more ASICs and/or FPGAs. Alternatively or in addition to the above, the processor may include or may be associated with a tangible and non-transitory memory having stored thereon instructions configured to direct the processor to perform the algorithms described herein.

It is noted that operations performed by the processor (e.g., operations corresponding to the methods/algorithms described herein, or aspects thereof) may be sufficiently complex that the operations may not be performed by a human being within a reasonable time period based on the intended application of the assay system. The processor may be configured to receive signals from the various subsystems and devices of the system or user inputs from the user. The processor may be configured to perform the methods described herein.

Processors may include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system 400.

In an exemplary embodiment, the processor executes a set of instructions that are stored in one or more storage elements, memories, and the like. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the system to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:
    a gantry defining a bore configured to accept an object to be imaged;
    a plurality of detector units coupled to the gantry, the detector units being configured to face toward a center of the bore and having respective detector field-of-views (FOVs), each of the detector units configured to rotate about a unit axis, the plurality of detector units including a series of first detector units and a second detector unit;
    at least one processor configured to execute programmed instructions stored in memory, wherein the at least one processor, when executing the programmed instructions, performs the following operations:
        rotate the first detector units such that the first detector units face in a common first direction that is generally toward the bore, wherein a working gap exists between the detector FOVs of the respective first detector units; and
        rotate the second detector unit such that the second detector unit faces in a second direction that is opposite the first direction, the detector FOV of the second detector unit covering the working gap.

2. The system of claim 1, wherein the at least one processor is configured to acquire image data from the first detector units and the second detector unit and generate a composite persistence image based on the image data.

3. The system of claim 1, wherein the plurality of detector units include a series of the second detector units.

4. The system of claim 3, wherein the first detector units define a plurality of the working gaps, the detector FOVs of the second detector units including the working gaps.

5. The system of claim 1, wherein a central longitudinal axis extends through the bore of the gantry, the plurality of detector units being configured to rotate as a group about the bore between first and second rotational positions, the second detector unit including the working gap when in the first rotational position, the second detector unit excluding the working gap when in the second rotational position.

6. The system of claim 1, wherein a central longitudinal axis extends through the bore of the gantry, the plurality of detector units being configured to rotate as a group about the bore between first and second rotational positions, wherein a working void exists between the detector FOV of the second detector unit and at least one of the detector FOVs of the first detector units when the plurality of detector units are in the first rotational position, the at least one processor configured to rotate the plurality of detector units to the second rotational position, wherein at least one of the detector FOVs of the first detector units or of the second detector unit includes the working void in the second rotational position.

7. The system of claim 1, wherein the plurality of detector units includes a series of third detector units and a fourth detector unit, the at least one processor configured to:
    rotate the third detector units such that the third detector units face in a common third direction that is generally toward the bore, wherein a working gap exists between the detector FOVs of the respective third detector units; and rotate the fourth detector unit such that the fourth detector unit faces in a fourth direction that is opposite the third direction, the detector FOV of the fourth detector unit including the working gap between the detector FOVs of the respective third detector units.

8. The system of claim 7, wherein the at least one processor is configured to acquire image data from the first detector units, the second detector unit, the third detector units, and the fourth detector unit, the at least one processor configured to generate first and second composite persistence images based on the image data, the first and second composite persistence images being of respective anatomical planes that are perpendicular to each other.

9. A method of imaging an object within a bore of a nuclear medicine (NM) imaging system, the NM imaging system including a plurality of detector units that are distributed about the bore and that each include a detector field-of-view (FOV), the plurality of detector units including a first series of first detector units and a second detector unit, the method comprising:
    positioning an object onto a table within the bore of the NM imaging system and moving the table to a designated position, wherein, using at least one processor, the method further comprises:
        rotating the first detector units to face in a common first direction that is generally toward the bore, wherein a working gap exists between the detector FOVs of the respective first detector units;
        rotating the second detector unit to face in a second direction that is opposite the first direction, the detector FOV of the second detector unit including the working gap; and
        acquiring image data from the first and second detector units and generating a composite persistence image based on the image data; and
    adjusting the position of the table within the bore based on the composite persistence image.

10. The method of claim 9, wherein the detector units include a series of the second detector units and wherein the first detector units form a plurality of the working gaps, the detector FOVs of the second detector units including the working gaps.

11. The method of claim 9, wherein adjusting the position of the table includes automatically adjusting the position using the at least one processor or receiving user inputs to move the table.

12. The method of claim 9, wherein a central longitudinal axis extends through the bore of the gantry, the method further comprising rotating the plurality of detector units as a group about the bore between first and second rotational positions, the second detector unit including the working gap in the first rotational position, the second detector unit not including the working gap in the second rotational position.

13. The method of claim 9, wherein a central longitudinal axis extends through the bore of the gantry, the method further comprising:
    rotating the plurality of detector units as a group about the bore to a first rotational position, wherein a working void exists between the detector FOV of the second detector unit and at least one of the detector FOVs of the first detector units when the plurality of detector units are in the first rotational position; and
    rotating the plurality of detector units as a group to a second rotational position, wherein at least one of the detector FOVs of the second detector unit or of the first detector units includes the working void in the second rotational position.

14. The method of claim 9, wherein the plurality of detector units includes a third series of third detector units and a fourth detector unit, the at least one processor configured to:
    rotate the third detector units such that the third detector units face in a common third direction that is generally toward the bore, wherein a working gap exists between the detector FOVs of the respective third detector units; and
    rotate the fourth detector unit such that the fourth detector unit faces in a fourth direction that is opposite the third direction, the detector FOV of the fourth detector unit including the working gap between the detector FOVs of the respective third detector units; and
    generate a composite persistence image based on the image data from the third detector units and the fourth detector unit.

15. The method of claim 14, wherein the composite persistence image based on the image data from the first detector units and the second detector unit includes a first anatomical plane and the composite persistence image based on the image data from the third detector units and the fourth detector unit includes a second anatomical plane that is perpendicular to the first anatomical plane.

* * * * *